(12) United States Patent
Lattner et al.

(10) Patent No.: US 9,126,882 B2
(45) Date of Patent: Sep. 8, 2015

(54) HYDROCARBON PYROLYSIS METHOD

(71) Applicants: James R. Lattner, Laporte, TX (US); Paul F. Keusenkothen, Houston, TX (US); Frank Hershkowitz, Basking Ridge, NJ (US)

(72) Inventors: James R. Lattner, Laporte, TX (US); Paul F. Keusenkothen, Houston, TX (US); Frank Hershkowitz, Basking Ridge, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 180 days.

(21) Appl. No.: 13/735,365

(22) Filed: Jan. 7, 2013

(65) Prior Publication Data

US 2013/0211165 A1     Aug. 15, 2013

Related U.S. Application Data

(60) Provisional application No. 61/597,383, filed on Feb. 10, 2012.

(51) Int. Cl.
*C07C 4/04* (2006.01)
*C07C 5/327* (2006.01)
*B01J 8/02* (2006.01)
*C07C 2/78* (2006.01)

(52) U.S. Cl.
CPC ............... *C07C 5/327* (2013.01); *B01J 8/0292* (2013.01); *C07C 2/78* (2013.01)

(58) Field of Classification Search
USPC ................... 585/535, 324, 325, 650
See application file for complete search history.

(56) References Cited

U.S. PATENT DOCUMENTS

| | | | |
|---|---|---|---|
| 2,186,590 A | 3/1936 | Martin et al. | |
| 2,139,679 A | 12/1938 | Hardy | |
| 2,319,679 A * | 5/1943 | Hasche et al. | 585/535 |
| 7,544,852 B2 | 6/2009 | Stell et al. | |
| 7,943,808 B2 | 5/2011 | Hershkowitz et al. | |
| 8,013,196 B2 | 9/2011 | Mamedov et al. | |
| 2005/0065392 A1 | 3/2005 | Peterson et al. | |
| 2011/0008226 A1 | 1/2011 | Hershkowitz et al. | |

FOREIGN PATENT DOCUMENTS

EP     1741691     1/2007

* cited by examiner

*Primary Examiner* — Thuan D Dang

(57) ABSTRACT

Disclosed is a pyrolysis reaction process. The process can be advantageously accomplished using a pyrolysis reactor that has a primary reaction zone comprised of bed packing having multiple passages through the bed packing and a secondary reaction zone having an open flow arrangement. The process includes a step of injecting a pyrolysis feed comprising a first hydrocarbon into the primary reaction zone to produce a primary pyrolysis product containing unsaturated hydrocarbon. A reactive feed comprising a second hydrocarbon is injected into the secondary reaction zone to mix with the primary pyrolysis product and produce a secondary pyrolysis product.

16 Claims, 7 Drawing Sheets

HYDROCARBON PYROLYSIS METHOD

CROSS-REFERENCE TO RELATED APPLICATIONS

The present application is related to, and claims priority to, U.S.S.N. Application No. 61/597,383, filed on Feb. 10, 2012 and entitled, "Hydrocarbon Pyrolysis Method," the disclosure of which is hereby incorporated by reference herein.

FIELD OF THE INVENTION

This invention relates to a process for pyrolysing hydrocarbon to produce a product containing unsaturated hydrocarbon. In particular, this invention relates to a process for pyrolysing hydrocarbon to produce a product containing substantial quantities of unsaturated hydrocarbon, such as alkynes, alkenes, or mixtures thereof.

BACKGROUND OF THE INVENTION

Pyrolysis reactors have been used in refineries or chemical plants to produce olefinic materials (e.g., ethylene and propylene) from various hydrocarbon feeds for petrochemicals manufacture. The feeds for this type of reactor typically range from ethane to vacuum gas oil, with heavier feeds giving higher yields of additional by-products, such as naphtha.

Pyrolysis reactors have also been used to produce alkynes, such as acetylene. As an example, U.S. Pat. No. 7,943,808 describes a reverse-flow regenerative reactor utilized in the manufacture of acetylene and other higher hydrocarbons from a methane feed. This type of reactor uses a series of bed packings to heat up and quench streams passing through the reactor. However, this process relied upon the bed packings to provide the quench (e.g., via indirect quenching).

As an alternative approach, U.S. Pat. No. 2,319,679 to Hasche describes a pyrolysis reactor that can be used to produce acetylene containing product at low pressure. In this process, the reactor is a regenerative reverse flow type reactor, which stores heat in tiles or bricks for carrying out the pyrolysis of the methane feed. Then, the feed is quenched with a water quench after passing through a single bed packing of bricks or tiles. In this process, longer cycles are utilized for the heating step and the pyrolysis step, which are two or more minute cycles. Disadvantageously, these longer cycles result in lower selectivity and increased buildup of tar and coke within the reactor, which is difficult to remove based at least on the extended exposure to heat.

U.S. Pat. No. 8,013,196 to Mamedov describes a two-stage pyrolysis scheme that is used to convert methane containing feed to acetylene. The acetylene is then in situ hydrogenated into ethylene using a higher alkane as a hydrogen transfer medium. Oxygen is fed to the pyrolysis reactor along with the methane to produce a combustion reaction in the pyrolysis reactor. As a result of the oxygen co-feed, substantial amounts of $H_2O$ and CO are produced in the pyrolysis product. These undesired byproducts have to be separated from the desired products, which increase the complexity and costs associated with the process. Further, the substantial amounts of $H_2O$ and CO react with the hydrocarbons to lessen the efficiency of the process.

There is a desire to enhance pyrolysis reaction processes to produce greater quantities of unsaturated hydrocarbons, and lesser quantities of undesired by-products, such as $H_2O$, CO, and $CO_2$. In particular, there is a desire to produce quantities of unsaturated hydrocarbons, such as acetylene, that can be readily converted to ethylene. As economics tends to further favor heavier feeds for pyrolysis processes, there is also a desire to develop enhanced pyrolysis processes that are more readily capable of handling a wider variety of hydrocarbon feeds than conventional processes. There is also a desire for enhancing pyrolysis reaction processes to increase the production of acetylene and/or ethylene in the pyrolyzed product, while also reducing the problems associated with coke and tar build-up. Furthermore, there is a desire to convert some of the acetylene product to ethylene within the pyrolysis reactor, as this reduces the complexity of the downstream processes to convert acetylene to ethylene, when ethylene is the desired product.

SUMMARY OF THE INVENTION

This present invention provides an enhanced pyrolysis reaction process that produces substantial quantities of unsaturated hydrocarbons, and lesser quantities of undesired by-products, such as $H_2O$, CO, and $CO_2$. In particular, the process produces substantial quantities of unsaturated hydrocarbons, such as ethylene, as well as unsaturated hydrocarbons, such as acetylene, that can be readily converted to ethylene. The pyrolysis reaction may also be performed to increase production of ethylene in the pyrolyzed product or reactor product by various techniques, such as higher pressure operation, actively managing the quench, use of reactive quench and/or the combination of hydrogen with the pyrolysis feed. Further still, the process can also enable a reduction in coke and tar build-up in particular portions of the pyrolysis reactor.

In one or more embodiments, a method for pyrolyzing hydrocarbon in a regenerative pyrolysis reactor, the reactor having (i) a mixing zone, (ii) a primary reaction zone, and (iii) a secondary reaction zone, is described. The method comprises the steps of: providing combustion reactants to the mixing zone, the mixing zone being adjacent a first end of a bed packing located in the primary reaction zone; during a first time interval, reacting the combustion reactants to produce heat and combustion products; passing the combustion products through a plurality of passages in the bed packing from the first end to a second end to transfer heat to the bed packing, wherein the bed packing has a plurality of passages through the bed packing from the first end to a second end; conducting away the combustion products from the second end of the bed packing; providing a pyrolysis feed comprising a first hydrocarbon to the second end of the bed packing; and during a second time interval, exposing at least a portion of the pyrolysis feed to peak pyrolysis gas temperatures≥1500° C. and at a pressure of ≥248 kPag as the pyrolysis feed passes through the bed packing from the second end to the first end to produce a primary pyrolysis product containing unsaturated hydrocarbon, wherein (i) second time interval is less than the first time interval and (ii) the first time interval and the second time interval are combined to be within the range of 1 to 60 seconds.

In one or more embodiments, a regenerative reactor system is described. The system may include a reverse flow regenerative reactor comprising: a housing enclosing an interior region; a bed packing disposed within the interior region and having a plurality of flow passages through the bed packing; one or more pyrolysis poppet valves configured to manage the flow of pyrolysis streams between a location external to the interior region and a location within the interior region; one or more combustion poppet valves configured to manage the flow of combustion streams between a location external to the interior region and a location within the interior region; and a reactive feed distribution device configured to manage the flow of a reactive stream between a location external to the interior region and a location within the interior region. The pyrolysis reactor may be at a pressure in the range of 248 kPag to 2068 kPag, or in the range of 303 kPag to 1124 kPag.

In one or more embodiment, the method and/or system may include other aspects. For instance, a reactive feed comprising a second hydrocarbon may be injected into a secondary reaction zone to mix with the primary pyrolysis product and produce a secondary pyrolysis product, wherein the secondary pyrolysis product has an ethylene concentration greater than that of the primary pyrolysis product; and removing the secondary pyrolysis product from the regenerative pyrolysis reactor. The reactive feed comprises at least 50 wt % ethane, based on total weight of the reactive feed and may be provided at a temperature≥500° C. Also, the reactive feed may be injected into the pyrolysis reactor and the pyrolysis feed is provided to the reactor at a respective mass flow ratio of from 0.5:1 to 2.0:1, based on the mass of the hydrocarbon in the reactive feed and pyrolysis feed. Moreover, the sum of the first time interval and the second time interval is in the range of 1 to 30 seconds or in the range of 1 to 15 seconds.

Further, other variations to the embodiments may be utilized. For instance, the unsaturated hydrocarbon in the secondary pyrolysis product may be comprised of >50 wt % ethylene compounds, based on total weight of the unsaturated hydrocarbon. Also, the secondary pyrolysis product comprises of ethylene and acetylene at a respective mass ratio of ≥1.5:1 based on the weight percentage of ethylene and acetylene in the secondary pyrolysis product. The first hydrocarbon and the second hydrocarbon are different mixtures of hydrocarbons. Further, the primary pyrolysis product has an ethylene to acetylene (E/A) weight ratio≥0.2 and the primary pyrolysis product is exposed to a peak pyrolysis gas temperature of at least 1600° C. Also, the secondary pyrolysis product is exposed to a peak pyrolysis gas temperature that is less than the peak pyrolysis gas temperature at which the primary pyrolysis product is exposed.

In still other embodiments, the products may be quenched at different locations. For example, the secondary pyrolysis product may be contacted with a quench fluid to cool the secondary pyrolysis product. Also, the primary pyrolysis product may be contacted with a quench fluid to cool the primary pyrolysis product.

Further, other embodiments may include different equipment configurations. For example, the reverse flow regenerative reactor may include one or more mixing components disposed within the internal region and between at least one or more combustion poppet valves and the bed packing, or one or more baffles disposed between the at least one combustion poppet valve and the bed packing, wherein the baffles have a plurality of flow passages. Also, the system may include at least one heat exchanger disposed downstream of the pyrolysis reactor and configured to cool the reactor effluent via indirect heat exchange, at least one quench medium distributor disposed between the heat exchanger and the pyrolysis reactor and configured to inject a quenching medium into the reactor effluent, and/or at least one quench medium distributor disposed downstream of the heat exchanger and configured to inject a quenching medium into the cooled reactor effluent. The system may also include a burner in fluid communication with the interior region and configured to: i) during a heating step, receive fuel and oxidant from the two or more combustion poppet valves, wherein the fuel and oxidant are provided from different poppet valves, and provide a passage for at least a portion of the fuel and oxidant to the interior region; ii) during the pyrolysis step, receive a reactive feed from the reactive feed distribution device and provide a passage for at least a portion of the reactive feed stream to the interior region. Moreover, the reactive feed distribution device may be configured to manage the flow of fuel streams and reactive streams between a location external to the interior region and a location within the interior region.

Figure 1:
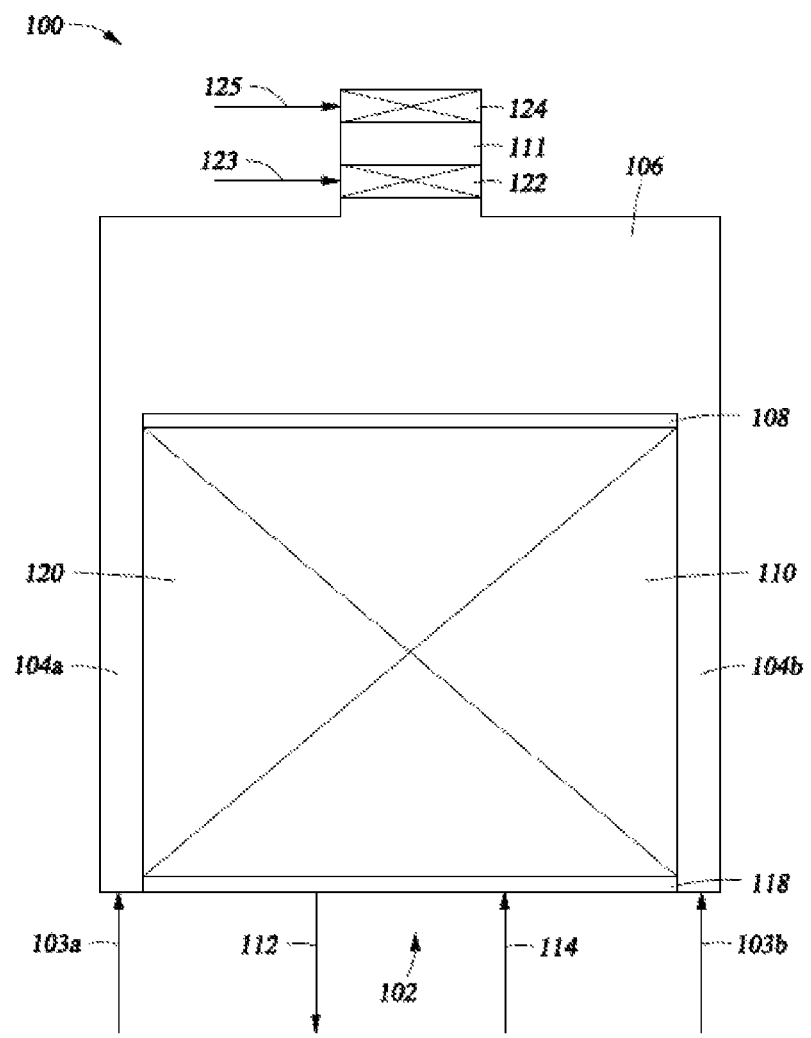
FIG. 1 is a simplified schematic diagram of one exemplary embodiment of a thermal pyrolysis process in which the thermal pyrolysis reaction is carried out in a regenerative reverse-flow reactor.

Although the invention can be described in terms of a pyrolysis process for producing acetylene and ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE INVENTION

I. Introduction

The present invention is directed to a thermal pyrolysis process that produces higher concentrations of unsaturated hydrocarbon relative to comparable processes. The pyrolysis reaction can be advantageously accomplished using a pyrolysis reactor that has a primary reaction zone comprised of bed packing having a plurality of passages (e.g., two or more passages) through the bed packing. The pyrolysis reactor may be operated in a manner that utilizes higher pressures to enhance the production of ethylene. The higher reactor pressures may be utilized to produce higher alkene concentrations. These reactor pressures may include pressures greater than or equal to (≥) 36 pounds per square inch gauge (psig) (248 kilo Pascal gauge (kPag)), ≥44 psig (303 kPag), or ≥103 psig (710 kPag).

Further, the process may utilize the shorter cycle times for the heating (e.g., regeneration) and pyrolysis steps to further manage the tar and coke formation within the reactor. The cycle times, which may be divided into different time intervals for each step, such as a first time interval for heating and a second time interval for pyrolysis, may be in the range of 1 to 60 seconds, in the range of 1 to 30 seconds, in the range of 1 to 15 seconds, or in the range of 1 to 6 seconds. By utilizing the shorter cycle times, the tar and coke within the reactor may be removed more efficiently. Further, the reduced yields of coke lead to enhanced heat transfer and therefore higher efficiency. Also, because coke is not heated in the longer cycle, it is easier to remove in subsequent steps.

As yet another enhancement, the process may involve managing the quenching of the pyrolysis products through various mechanisms. For instance, the process may include quenching the pyrolysis product with a quenching fluid, the quenching fluid being, e.g., a non-reactive feed and/or a reactive feed. The addition of another fluid downstream of the primary reaction zone serves to reduce the temperature of the mixture, which may be managed to control the quenching process. This quench fluid may be provided in one or more staged steps along the flow path. A non-reactive quench feed or fluid may not undergo significant reaction when mixed with the hot gas stream (the pyrolysis stream or effluent from the bed packing), while a reactive feed or fluid undergoes significant hydrocarbon conversion reaction when mixed with the hot gas stream. The reactions that occur with a reactive feed include endothermic pyrolysis reaction of the reactive species (e.g., conversion of ethane to ethylene plus hydrogen, and/or interconversion reactions involving the exchange of hydrogen between species (e.g., the reaction of ethane with acetylene to form two ethylenes).

As an example, the non-reactive quench fluid may be utilized before and/or after the reactive feed to manage the quenching of the pyrolysis products to reduce undesired byproducts, while still providing conversion of hydrocarbons in the reactive feed. As an embodiment, the process may include injecting a reactive feed into the primary pyrolysis products downstream of the bed packing to convert a portion of the reactive feed and a portion of the primary pyrolysis products into desired products (e.g., ethylene). This injection of the reactive feed may also cool the primary pyrolysis products to hinder the over-conversion of the pyrolysis products. The reactive feed may be injected in a secondary reaction zone having an open flow arrangement (e.g., a void space or open region within the reactor) that is downstream of the primary reaction zone or overlaps with at least a portion of the primary reaction zone.

In one or more embodiment, the method may include a step of injecting a pyrolysis feed comprising a first hydrocarbon into the primary reaction zone, which may include the bed packing, to produce a primary pyrolysis product containing unsaturated hydrocarbon. A reactive feed comprising a second hydrocarbon may then be injected into a secondary reaction zone to combine the primary pyrolysis product with the reactive feed and produce a secondary pyrolysis product. The reactive feed serves to cool the primary pyrolysis product, while allowing additional pyrolysis to be continued inside the secondary reaction zone. As a result, the secondary pyrolysis product that is produced from the secondary reaction zone, it may have an alkene concentration greater than that in the primary pyrolysis product. That is, the alkene (e.g., ethylene) concentration may be greater in the secondary pyrolysis product than in the primary pyrolysis product (on a weight percentage basis). The secondary pyrolysis product may also have an alkyne (e.g., acetylene) concentration that is less than that the alkyne concentration in the primary pyrolysis product. The secondary pyrolysis product can be directly removed from the secondary reaction zone of the pyrolysis reactor and optionally cooled with a non-reactive quench fluid. The non-reactive quench fluid may also be introduced upstream of the reactive feed, to manage the temperature of the stream (e.g., pyrolysis product) as the reactive feed is introduced.

The present aspects are particularly beneficial in producing a secondary or final pyrolysis product that has substantial quantities of unsaturated hydrocarbons, and lesser quantities of undesired by-products such as $H_2O$, CO, and $CO_2$ relative to previous pyrolysis processes. This process enables increased production of ethylene in the secondary pyrolysis product, as compared to other processes. Any remaining acetylene in the secondary pyrolysis product can be selectively hydrogenated in an additional hydrogenation step to produce additional quantities of ethylene, which can then serve as feed stock to any of a variety of chemical processing units, such as oligomerization or polymerization processes.

II. Pyrolysis Reactor

A reactor refers to equipment used for chemical conversion. As such, several items identified as reactors may be combined to become a single entity that is also identified as a reactor, in that individual and combined entities may be characterized as equipment used for chemical conversion.

The process of the present techniques is carried out in a pyrolysis reactor. A pyrolysis reactor refers to equipment for converting hydrocarbons by means of at least pyrolysis chemistry. The pyrolysis reactor may include one or more reactors and/or associated equipment and lines. In certain embodiments, the pyrolysis reactor may include one reactor bed (e.g., one reactor bed, or two or more reactor beds disposed directly adjacent to each other and substantially forming a single bed packing). Such a reactor is preferably a single stage reactor bed having a single primary reaction zone within the reactor, which is followed by a mixing zone or open volume within the reactor. An example of such a reactor configuration is shown in U.S. Pat. No. 2,319,679 to Hasche, as discussed above.

Reverse-flow regenerative reactor is (i) "reverse flow" in the sense that upstream region of the reactor with respect to the average flow of a pyrolysis stream is the downstream region with respect to the average flow of another stream (e.g., combustion streams) and (ii) is "regenerative" in the sense that at least a portion of the heat consumed during the conversion of the pyrolysis stream is provided by exothermically reacting the other stream. Regenerative reactor being a reactor that performs sequential steps in a cycle of reacting fuel and oxidant to store heat within a defined volume in a heating step and removing a portion of the heat during the conversion of a feed stream in a conversion step. For example, under thermal pyrolysis conditions, the regenerative reactor exothermically react fuel and oxidant to store heat within a bed packing in the reactor (e.g., reactor bed) in a heating step and removes a portion of the heat during the conversion of a pyrolysis stream in a pyrolysis step. The heating step may be in first time interval, while the pyrolysis step is performed in a second time interval, which may be the same or shorter than the first time interval.

Preferably, the reverse-flow regenerative reactor includes a first end in which a pyrolysis feed comprising a first hydrocarbon is injected into a primary reaction zone and a second end near or adjacent to a mixing zone and/or a secondary reaction zone. The primary reaction zone may comprise a bed packing and one or more different flow distribution devices. The bed packing may include a monolith or particulate packing (e.g., solid material having multiple passages or flow channels through the material). The material of the bed packing acts as a heat transfer and/or storage material in which sufficient heat can be transferred to the stream (e.g., pyrolysis feed) to carry out the desired pyrolysis reaction.

The reactor may also include a partial quench, a secondary reaction zone downstream or even immediately downstream of the primary reaction zone with a reactive feed distribution device. The reactive feed distribution device may include a mixing unit, a sparger, or conduit with orifices, valves and/or nozzles, or other suitable devices. A reactive feed comprising a second hydrocarbon, which is described further below, is injected into the secondary reaction zone to intermingle the reactive feed with the primary pyrolysis product at a lower temperature than the bed packing and that is sufficient to carry out a secondary pyrolysis reaction and produce a secondary pyrolysis product.

This secondary reaction zone can comprise of an open flow volume or open channel with the reactive feed distribution device disposed along surfaces defining the open flow volume or within the open flow volume. The open flow volume means that the secondary reaction zone has a relatively open reaction zone, being devoid of other solid or flow diverting structures (e.g., heat exchange channels or passages). This open flow volume of the secondary reaction zone may preferably be disposed near a second end of the bed packing downstream of the flow path of the pyrolysis stream relative to the bed packing.

Within the reactor, pyrolysis or pyrolysis chemistry involves the conversion of is hydrocarbons to unsaturates, such as ethylene and acetylene, which is an endothermic reaction requiring addition of heat. The terms "crack" and "cracking" may be used interchangeably with the terms pyrolyze and pyrolysis. In a pyrolysis reaction, ≥50%, ≥80%, or ≥90%, of this heat is provided by heat transfer via solid surfaces, such as tubulars or bed materials. Any combustion chemistry that occurs within the pyrolysis reactor provides a minority of the endothermic heat of pyrolysis of the pyrolysis stream, such as <50%, <20%, or <10% of the endothermic heat of pyrolysis. Accordingly, thermal pyrolysis is generally defined as a thermal decomposition process in which the pyrolysis stream is heated, generally in the absence of minimal oxygen, to decompose hydrocarbons in the pyrolysis stream into unsaturated hydrocarbon molecules. The pyrolysis product produced from passing the pyrolysis stream (e.g., pyrolysis feed, which is described further below) through the reactor includes unsaturated hydrocarbon in which a substantial amount of the unsaturated hydrocarbon preferably includes alkyne compounds, such as acetylene.

A zone, as used herein, refers to a location within the pyrolysis reactor, which may include one or more reactors and/or associated equipment and lines. The zone may include a specific volume within a reactor and/or the combination of different disjointed volumes in the reactor. In one embodiment, the thermal pyrolysis reverse-flow regenerative reactors described herein may comprise a single reactor bed, which may include one or more bed packing materials, wherein the primary reaction zone and the secondary reaction zone are adjacent zones within the interior of the reactor. Further, in other embodiments, the pyrolysis reactor may consist of a primary reaction zone and a secondary reaction zone, with the primary reaction zone comprising a bed packing and including a first end and a second end of the bed packing, while the secondary reaction zone may be disposed downstream of the primary reaction zone or overlap with the primary reaction zone downstream of the injection of the reactive feed and/or downstream of the bed packing. That is, the secondary reaction zone receives the primary pyrolysis product, which may include unreacted pyrolysis stream and pyrolysis products.

The primary reaction zone is a location in the thermal pyrolysis system where >50%, >75%, and/or >90% of the conversion of hydrocarbons in the pyrolysis feed into $C_{2+}$ unsaturates is performed. That is, while some thermal cracking may occur downstream of the primary reaction zone in the secondary reaction zone, the primary reaction zone is the location or volume within the reactor where a substantial amount of the smaller molecules are produced from the initial hydrocarbons provided in the pyrolysis feed to the primary reaction zone.

In certain pyrolysis reactors (e.g., steam cracking furnace configuration), the heating and the pyrolysis process occur simultaneously, for example with a combusting stream on one side of partition (typically a wall or tubular) and the pyrolysis stream on the other side. Such reactors operate at or near steady state. The partition between the combustion stream (e.g., reactants used during a heating step) and the pyrolysis stream has real physical dimensions and the temperature is not equal at every location. For example, on the combustion side, temperatures may be hottest near a flame region (e.g., burner), and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the reactions and heat transfer that takes place in the reactor.

The term "peak pyrolysis gas temperature" means the maximum temperature achieved by the bulk pyrolysis stream gases (e.g., portion of the pyrolysis stream passing through the reactor) as they travel through the pyrolysis reactor (e.g., primary reaction zone). One skilled in the art appreciates that temperatures immediately proximate to the partition or channel walls within the primary reaction zone may be higher, and may, in some infinitesimal layer, actually approach the solid temperature. However, the pyrolysis temperature referred to herein should be considered a bulk gas temperature, which is a temperature that could be measured by a device (such as a thermocouple) that is not in contact with the bed packing. For example, if the gas is traveling through tubulars in a primary reaction zone of a thermal pyrolysis reactor, the bulk gas temperature may be taken as the average temperature over any tubular cross-section, and the peak pyrolysis gas temperature as the highest cross-sectional-average temperature of the pyrolysis stream in the primary reaction zone.

In certain embodiments, a cyclical process may be utilized that involves repeating a heating step, pyrolysis step and any other steps, if any, in each cycle, as part of the hydrocarbon processing mode. The process may include various steps during a hydrocarbon processing mode and a non-operational mode. The hydrocarbon processing mode may refer to the steps utilized by the reactor system to convert hydrocarbons in the feed into useful products, such as $C_2$ unsaturates. For instance, as noted above, the steps in a cyclical process of the hydrocarbon processing mode may involve repeating a heating step, a pyrolysis step and any other steps, if any, in each cycle. These steps may include a flushing step and/or heating step that removes at least a portion of the non-volatiles from the reactor as part of the cycle. Alternatively, a non-operation mode may be utilized for reactor cleaning operations. The non-operational mode typically involves interrupting the flow of hydrocarbons to decoke the reactor, where decoking refers to removal of at least a portion of coke deposited on various surfaces of the reactor system.

The cycle may be performed continuously, semi-continuously, or even as a batch operation. Accordingly, a cycle includes the time spent in the heating step plus time spent in the primary and secondary pyrolysis steps plus any time needed to switch between steps or for additional steps before the repeat of the sequence. Typical cycle times may be in the range of 1 to 60 seconds, in the range of 1 to 30 seconds, in the range of 1 to 15 seconds, or in the range of 1 to 6 seconds. The heating and pyrolysis steps may each have equal durations or may be adjusted to have different durations. The cycle time may be shorter than other published cycle times to avoid a significant build-up of coke and/or tar in the primary reaction zone, which can also be subsequently swept away in the transitional steps and/or the heating step. Further, the cycle time may be a combination of a first time interval (e.g., heating step time interval) and the second time interval (e.g., the pyrolysis time interval).

For a reverse-flow regenerative reactor, the process may include a heating step to heat the primary reaction zone, particularly to heat the bed packing material in the primary reaction zone, and a pyrolysis step that converts the hydrocarbons into the pyrolysis products (e.g., reactor product). The steps, which are described further below, may involve passing the respective streams over a bed packing, in which the bed packing is in a fixed orientation within the primary reaction zone. The reactor incorporates valves to alternate introduction of streams (e.g., the pyrolysis feed and/or combustion feed or reactants) into the internal region of the reactor, and to contact the bed packing of the primary reaction zone. As an example, this process may include flowing streams in a single direction through the primary reaction zone in one or more steps and reversing the flow of the streams in the opposite direction in one or more additional steps.

The heating step involves mixing a fuel stream with the main oxidizing stream flowing in one direction, while the quench step involves mixing a quench stream (either reactive or non-reactive) with the pyrolysis product stream flowing the other direction. A distribution device may be advantageously utilized for both purposes, that is, to mix the fuel with oxidant during the heating step, and to also mix the quench stream with the pyrolysis product stream during the pyrolysis step.

The bed packing of the primary reaction zone may be designed to facilitate the process of heat addition and removal. Checker bricks, tiles, pebbles, and monoliths may be used as the bed packing within the reactor. Such materials form a network of passages that are used by the gases in each step to transit the region containing bed packing material. The heat addition step leaves a profile of temperatures in the bed packing material. That is, the temperature varies along the path by which the gases transit the material. The shape of that profile depends on many factors, including if and where a heat release (e.g., combustion) reaction occurs, the initial temperature distribution, the duration of the heating step, the flow rate and inlet temperature of the gas stream, and the heat capacity and transfer properties of the gas and bed packing material. On average, the bed packing is hottest at the end of the heating step. The primary pyrolysis step consumes heat and reduces average bed packing material temperature. The pyrolysis step changes the profile of temperatures in the bed packing material, in a way that depends on many factors, including where the heat consumption (pyrolysis) reaction occurs, the initial temperature distribution, the duration of the pyrolysis step, the flow rate and inlet temperature of the pyrolysis stream, and the heat capacity and transfer properties of the gas and solid. Fixed-solid regenerative pyrolysis reactors do not operate in the steady state. That is, at any given location, the temperature changes. However, these reactors may be in a periodic steady state, meaning that the same cycling of temperatures occurs over and over as the reactor sequentially repeats the heating and pyrolysis steps.

The bed packing material (e.g., heat storing and transferring material of the primary reaction zone) may be a ceramic, which may include yttria, zirconia, alumina, and/or other refractory material capable of withstanding temperatures within the pyrolysis reactor. In the present techniques, pyrolysis in the primary reaction zone may be carried out at peak pyrolysis gas temperatures of at least 1200° C., at least 1700° C., at least 2000° C., preferably at least 1400° C., at least 1500° C., or more preferably at least 1540° C. The peak pyrolysis gas temperature in the primary reaction zone may include temperatures from 1200° C. to 2200° C., from 1450° C. to 1700° C., from 1500° C. to 1675° C., or from 1540° C. to 1650° C. In some reactions, it may even be still more preferable to expose the pyrolysis feed stream to heat using very short residence times, such as ≤0.1 second, to a temperature in excess of 1600° C. When the pyrolysis feed comprises methane, the primary pyrolysis reaction typically includes peak pyrolysis gas temperatures in excess of 1400° C. for the methane to react or convert. An exemplary preferred process may pyrolyze the feed stream within the primary reaction zone, such as at peak pyrolysis gas temperatures of from 1540° C. to 2200° C., and more preferably from 1600° C. to 1800° C. Exemplary residence times in the primary reaction zone preferably may be short, such as ≤0.5 second, ≤0.3 second, and preferably ≤about 50 milliseconds or in the range of 0.5 seconds to 0.001 seconds.

The reactor can include, e.g., one or more conduits, channels, or passages. The term "conduit" refers to means for conducting a composition from one location to another. The term encompasses (i) elementary conducting means, such as a pipe or tube, and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, the channel having a plurality of passages or sets of passages, e.g., hundreds of thousands of passages per square meter of the honeycomb's cross-section.

These higher temperatures are utilized to crack feeds that are normally unreactive or react to low value products (e.g., degraded products) at lower temperatures. As a specific example, at temperatures≥1200.0° C., methane and aromatic components are partially cracked to yield unsaturated $C_2$+ compounds, typically acetylenes and ethylene. At temperatures≥1400.0° C. or preferably ≥1540.0° C., aromatics and methane may be cracked at high conversion levels, with selectivity levels≥50 wt % to light gas products. That is, at atmospheric pressure, higher temperature also provides selectivity to enhance the yield of unsaturated $C_2$+ compounds (e.g., yield of ethylene and acetylene). For example, the ethylene to acetylene weight ratio (E/A) can be ≤0.10 or as low as 0.02 at atmospheric pressure.

However, to further enhance the process, higher pressure may be utilized to increase the E/A for certain operating conditions. The present techniques utilize a thermal pyrolysis reactor configured to expose the pyrolysis feed to higher pressures than conventional thermal pyrolysis processes. These higher pressures are utilized to crack feeds at higher temperatures to yield higher conversions and selectivities to ethylene. As a specific example, at pressures≥36 psig (at peak pyrolysis gas temperatures≥1500° C.), methane and aromatic components are partially cracked to yield elevated levels of ethylene relative to lower pressures.

At any elevated temperature, hydrocarbon pyrolysis or hydropyrolysis produces acetylene at an intermediate residence time. As time continues, the hydrocarbons react further towards condensed species and eventually carbon (e.g., produce more coke). Thus, there is a maximum amount of acetylene, which is achieved at a specific residence time, and which is the optimum acetylene yield for a given temperature. The temperature and residence time of this maximum acetylene yield can be used to characterize thermal pyrolysis reactor performance at that temperature, in terms of the yield of $C_3^+$ in relationship to the yield of acetylene. The yield of $C_3^+$, as used herein, includes all $C_3^+$ products of the pyrolysis feed, whether those products emerge from the reactor or remain within the reactor as coke. $C_3^+$ includes, for example, products such as methyl acetylene, benzene and tar, and is specifically defined as including carbonaceous byproducts, such as coke. The variations of temperature are further described in U.S. Patent Ser. Nos. 61/434,409; 61/434,410; 61/434,411; 61/434,413; 61/434,415; 61/434,417; and 61/434,419, which are each incorporated by reference.

To enhance the yield of ethylene, variations in pressure along with the high-severity temperatures may enhance the distribution of $C_2$ compounds (e.g., yield of ethane, ethylene and acetylene) and the distribution of other light hydrocarbons (e.g., propylene, propyne, etc.). Accordingly, these pressure variations may be utilized if ethylene and/or other olefins are the preferred product. As an example, steam cracking typically utilizes lower temperature to convert ethane to ethylene and trace levels of acetylene. At atmospheric pressure, lower temperatures result in higher ethylene to acetylene (E/A) weight ratios. However, lower temperatures also provide poor conversions for methane and aromatics, which as noted above, is inefficient. At high-severity conditions (e.g., temperatures≥1400° C., or preferably ≥1540° C., for example) aromatics and methane may be cracked at high conversion levels, with selectivity levels≥50 wt % to light gas products. Also shown in Table A, at temperatures≥1400° C., selectivity levels≥50 wt % to light gas products are achievable. For example, at 1540° C., products of methane make up 67.8 wt % of the pyrolysis product, including $H_2$, $C_2$'s, and $C_3^+$. Thus, the selectivity to $C_3^+$ is 20 wt % (13.7 wt %/67.8 wt %), and the selectivity to lighter gas products is 80 wt %. Further, by varying the pressure from atmospheric to elevated pressures (e.g., up to 300 psig (2068 kPag)), ethylene to acetylene (E/A) weight ratios≥0.1, ≥0.2, ≥0.4, or even ≥0.5 may be achieved. The variations of pressure at high-severity operating conditions are described below in Tables A and B.

Table A includes simulation results for different ratios of reactor products produced at different pressures for different temperatures from a methane feed. Pyrolysis, in this example, is carried out under isothermal conditions at 1500° C. and at 1650° C., with 2:1 molar diluent of hydrogen in a methane feed, and at 15 psig (103 kPag) reactor pressure to 162 psig (1117 kPag) reactor pressure. All products larger than $C_2$ are considered as $C_3^+$ in this example and the product is the reaction product yield from the converted pyrolysis feed.

TABLE A

| 70% Isothermal Conversion Data | | | | | | | | | | | |
|---|---|---|---|---|---|---|---|---|---|---|---|
| Temp | P | Time | | Products (weight percent) | | | | | $C_3^+/$ | | |
| (° C.) | (psig) | (sec) | Conv. | $H_2$ | $CH_4$ | $C_2H_2$ | $C_2H_4$ | $C_3^+$ | $C_2U$ | $C_2U$ | E/A |
| 1500 | 15 | 0.025 | 72% | 31.1 | 22.0 | 34.2 | 2.0 | 10.7 | 36.0 | 0.30 | 0.06 |
| 1500 | 36 | 0.025 | 73% | 31.1 | 21.7 | 32.7 | 3.1 | 11.3 | 36.0 | 0.32 | 0.10 |
| 1500 | 44 | 0.025 | 72% | 31.0 | 22.1 | 31.9 | 3.5 | 11.5 | 35.0 | 0.33 | 0.11 |
| 1500 | 59 | 0.025 | 71% | 30.7 | 23.3 | 30.3 | 4.1 | 11.6 | 34.0 | 0.34 | 0.14 |
| 1500 | 74 | 0.025 | 69% | 30.4 | 24.7 | 28.6 | 4.6 | 11.7 | 33.0 | 0.35 | 0.16 |
| 1500 | 103 | 0.025 | 65% | 29.7 | 27.9 | 25.4 | 5.4 | 11.5 | 31.0 | 0.37 | 0.21 |
| 1500 | 162 | 0.025 | 57% | 28.4 | 34.3 | 20.3 | 6.3 | 10.8 | 27.0 | 0.41 | 0.31 |
| 1650 | 15 | 0.0025 | 68% | 30.4 | 25.4 | 35.0 | 1.0 | 8.2 | 36.0 | 0.23 | 0.03 |
| 1650 | 36 | 0.0025 | 71% | 30.8 | 23.6 | 35.6 | 1.5 | 8.5 | 37.0 | 0.23 | 0.04 |
| 1650 | 44 | 0.0025 | 71% | 30.8 | 23.3 | 35.6 | 1.7 | 8.6 | 37.0 | 0.23 | 0.05 |
| 1650 | 59 | 0.0025 | 71% | 30.9 | 22.9 | 35.4 | 2.0 | 8.7 | 37.0 | 0.23 | 0.06 |
| 1650 | 74 | 0.0025 | 71% | 30.9 | 22.8 | 35.2 | 2.3 | 8.8 | 37.0 | 0.24 | 0.07 |
| 1650 | 103 | 0.0025 | 71% | 30.8 | 22.9 | 34.4 | 3.0 | 8.9 | 37.0 | 0.24 | 0.09 |
| 1650 | 162 | 0.0025 | 70% | 30.5 | 24.0 | 32.5 | 4.1 | 9.0 | 37.0 | 0.25 | 0.13 |

As shown in Table A, as pressure increases from 15 psig (103 kPag) to 162 psig (1117 kPag), $C_2U$ yields in wt % of the product are roughly constant at about 33 wt % (+/−10 wt %) for 25 millisecond (ms) residence time at 1500° C. However, the E/A weight ratios improve over this increase in pressure. At 1650° C., the $C_2U$ yields in wt % of the product are again roughly constant at about 37 wt % (+/−10 wt %) for 2.5 ms, while the E/A weight ratio increases fourfold. Accordingly, the higher pressures tend to lead to higher E/A weight ratios. Further, the $C_3^+$ yields in wt % of the product at these different temperatures and pressures also remain relatively constant at 12% for 1500° C. and 9% for 1650° C. As a result, the $C_3^+$ to $C_2U$ weight ratio ($C_3^+/C_2U$) increases at slow rate with pressure at the lower temperature, while the higher temperatures provide a roughly constant $C_3^+$ to $C_2$ unsaturate weight ratio.

From this table, the yield of $C_2U$ (e.g., acetylene and ethylene) may be optimized for certain operating conditions. That is, a specific pressure, temperature, and residence time may be utilized to optimize the distribution of $C_2U$ yield. These operating conditions may be characterized by the $C_3^+$ to $C_2U$ weight ratio along with an E/A weight ratio.

Further, as it may be appreciated, different types of thermal pyrolysis reactors may have different heat profiles. That is, some embodiments of thermal pyrolysis reactors may operate in an isothermal manner with the heat profile being relatively constant, as noted above. However, other thermal pyrolysis reactors may have a heat profile that is similar to a Gaussian curve. For example, a regenerative reactor may be characterized by an initial and final temperature of 300° C. and a peak pyrolysis gas temperature of 1700° C. for a residence time of 35 ms (≤10 ms at temperature≥1000° C.), the pressure effect on selectivity is even more dramatic as shown in Table B below. In addition, a half reactor regenerative reactor (e.g., regenerative reactor that includes a single bed packing along with an active quench process) may be characterized by partial Gaussian curve and an initial temperature of 300° C. and a peak pyrolysis and final gas temperature of 1700° C. for a residence time of 35 ms (≤10 ms at temperature≥1000° C.); the pressure effect on selectivity is expected to be analogous for the half reactor as shown in Table B below.

The variations of pressure at high-severity operating conditions for a regenerative reactor are described below in Table B. Table B includes simulation results for different ratios of reactor products produced at different pressures for different temperatures from a methane feed. Pyrolysis, in this example, is carried out under regenerative conditions resulting in a Gaussian-like temperature profile with inlet and outlet around 300° C. and with peak temperature of 1704° C. in one set of simulations and of 1783° C. in the other. About 25% of the residence time of the regenerative pyrolysis profile is at temperature above 1200° C. The pyrolysis of this example is carried out with 2:1 molar diluent of hydrogen in a methane feed, and at various reactor pressures between 3 psig (21 kPag) and 162 psig (1117 kPag). All products larger than $C_2$ are considered as $C_3^+$ in this example and the product is the reaction product yield from the converted pyrolysis feed.

operating conditions may be characterized by the $C_3^+$ to $C_2U$ weight ratio along with an E/A weight ratio.

Although the E/A weight ratio continues to improve with increasing pressure, certain limiting factors may hinder higher pressure operations. For instance, eventually high pressure operating conditions may lead to unacceptable $C_3^+$ to $C_2U$ weight ratios and/or lower $C_2U$ yields. Further, equipment utilized in the system may be limited to certain pressure ranges. Accordingly, preferred operating pressures may include pressures≥36 psig (248 kPag), ≥44 psig (303 kPag) or ≥103 psig (710 kPag), but may be ≤300 psig (2068 kPag), 163 psig (1124 kPag), or ≤150 psig (1034 kPag). As may be appreciated, these different pressures may be combined together to form different combinations depending on the specific configuration of equipment.

In addition, it is beneficial to maintain longer residence times and lower temperatures to maximize E/A weight ratio. However, such residence times and temperatures result in higher weight ratios of $C_3^+$ to $C_2U$. Accordingly, the design and operating is conditions may be adjusted to provide a balance between the E/A weight ratio and the $C_3^+$ to $C_2U$

TABLE B

70% Regenerative Conversion Data

| Peak Temp (° C.) | Pres. (psig) | time (sec) | Conv. | Products (weight percent) | | | | | | $C_3^+/$ | |
|---|---|---|---|---|---|---|---|---|---|---|---|
| | | | | $H_2$ | $CH_4$ | $C_2H_2$ | $C_2H_4$ | $C_3^+$ | $C_2U$ | $C_2U$ | E/A |
| 1704 | 3 | 0.034 | 70% | 30.4 | 24.3 | 34.3 | 3.0 | 7.9 | 37.3 | 0.21 | 0.09 |
| 1704 | 15 | 0.034 | 72% | 30.7 | 22.2 | 33.6 | 5.0 | 8.4 | 38.6 | 0.22 | 0.15 |
| 1704 | 29 | 0.034 | 74% | 30.7 | 21.2 | 31.6 | 7.4 | 8.8 | 39.0 | 0.23 | 0.24 |
| 1704 | 36 | 0.034 | 74% | 30.6 | 21.0 | 30.5 | 8.5 | 8.9 | 39.0 | 0.23 | 0.28 |
| 1704 | 59 | 0.034 | 74% | 30.3 | 21.1 | 26.8 | 11.6 | 9.2 | 38.4 | 0.24 | 0.43 |
| 1704 | 103 | 0.034 | 71% | 29.4 | 23.1 | 20.1 | 15.6 | 9.1 | 35.7 | 0.26 | 0.78 |
| 1704 | 162 | 0.034 | 66% | 28.1 | 27.5 | 13.5 | 17.2 | 8.6 | 30.7 | 0.28 | 1.27 |
| 1783 | 15 | 0.011 | 67% | 30.0 | 26.5 | 33.4 | 3.0 | 7.1 | 36.3 | 0.20 | 0.09 |
| 1783 | 36 | 0.011 | 69% | 30.2 | 24.5 | 32.5 | 5.0 | 7.6 | 37.5 | 0.20 | 0.15 |
| 1783 | 44 | 0.011 | 70% | 30.2 | 24.2 | 31.9 | 5.8 | 7.8 | 37.6 | 0.21 | 0.18 |
| 1783 | 74 | 0.011 | 70% | 30.1 | 23.7 | 29.4 | 8.3 | 8.0 | 37.7 | 0.21 | 0.28 |
| 1783 | 103 | 0.011 | 70% | 29.8 | 23.8 | 26.7 | 10.6 | 8.1 | 37.3 | 0.22 | 0.40 |
| 1783 | 162 | 0.011 | 69% | 29.2 | 25.0 | 21.8 | 13.9 | 8.1 | 35.6 | 0.23 | 0.64 |

As shown in Table B, as pressure increases from 3 psig (21 kPag) to 162 psig (1117 kPag), $C_2U$ yields decrease at a slow rate from 37 wt % to 31 wt % for a 33 ms residence time in a temperature profile that peaks at 1704° C. However, the E/A weight ratios increase rapidly with the increase in pressure. For the profile having peak temperature of 1784° C. and an 11 ms residence time, the $C_2U$ yields are roughly constant at about 37 wt %, while the E/A weight ratio again increases with increasing pressure. Accordingly, the higher pressures tend to lead to higher E/A weight ratios, while the $C_3^+$ levels at these different temperatures and pressures remain relatively constant at around 8 wt % for the two profiles. As a result, the $C_3^+$ to $C_2U$ weight ratio increases at slow rate for these different temperatures with the higher temperature providing roughly constant $C_3^+$ to $C_2U$ weight ratio, but the E/A weight ratio increases at a larger rate. Moreover, higher pressures do not have a significant impact on $C_3^+$ levels as the $C_3^+$ to $C_2U$ weight ratio remains almost constant, which is an enhancement over the isothermal reactors.

From this table, the regenerative reactor may be utilized to further optimize the yield of $C_2U$ (e.g., acetylene yield relative to the ethylene yield) for certain operating conditions. That is, a specific pressure, temperature and residence time may be utilized to optimize the distribution of $C_2U$ yield along with the heat or temperature profile of the reactor. These weight ratio. That is, the thermal pyrolysis reactor may be operated at lower temperatures to maximize the E/A weight ratio at an efficient and operable $C_3^+$ to $C_2U$ weight ratio. For instance, the operation of the pyrolysis unit and hence operating conditions may be optimized based on objectives for the pyrolysis unit performance. As an example, the operating conditions, such as the peak pyrolysis gas temperatures and/or pressure, of the thermal pyrolysis reactor may be adjusted based on an optimized value from an optimization function that comprises an ethylene to acetylene weight ratio and the $C_3^+$ to $C_2U$ unsaturate weight ratio. In another example, when the objective is a high E/A weight ratio, the pyrolysis reactor may be optimized by (i) using a regenerative reactor or other reactor having a partial Gaussian-like temperature profile, (ii) increasing design operating temperature to be above a minimum level needed to achieve an acceptably low value of $C_3^+/C_2U$ (which may be referred to as a coke operability limit), and then (iii) increasing design operating pressure as much as possible given other reactor and system constraints. In another example, if the objective is a product with a minimal E/A weight ratio, the reactor may be optimized by (i) using a reactor that gives a isothermal temperature profile, (ii) operating the reactor at the lower end of the preferred pressure range, such as from about 36 psig (248 kPag) to about 59 psig (407 kPag), and (iii) increasing temperature as much as possible within the reactor materials constraints.

The thermal pyrolysis reactor may be limited to certain pressures by various limitations. For instance, at higher pressures and constant residence times, mass density of the gas increases and thus requires higher heat transfer rates per unit of reactor volumes. This heat transfer rate may exceed the capability of the reactor internals or may lead to exceedingly small channels or exceedingly large numbers of channels per square inch (CPSI). Thus, these limitations may eventually lead to impractical reactor dimensions and impractically high levels of pressure drop.

Further, the process may be further enhanced by managing the quenching process through an active quench. As noted above, the temperature profile may be adjusted by injecting reactive feed and/or non-reactive fluid into the stream downstream of the bed packing. In this manner, the reactions may be lessened as compared to the use of a second bed packing. In particular, the process may use one or more stages to inject quench fluids into the stream to reduce stream temperature and utilize the temperature of the stream to provide additional reactions to the desired product, such as ethylene. As such, the use of an is active quenching process may be utilized to further enhance the conversion process.

In an embodiment, the bed packing in the primary reaction zone may include components comprised of yttria. The bed packing, which may be referred to as a reactor bed, of the primary reaction zone includes separate conduits for separately channeling flow of pyrolysis feed or regeneration fluid components (e.g., combustion stream components) through the bed packing. The separate flow channels in the reactor bed can further comprise flow barriers that effectively function as conduit walls to prevent cross flow or mixing of fluids between channels. The reactor bed preferably includes multiple channels, which may preferably be in parallel flow arrangement.

In a particular embodiment, a channeled reactor bed of the primary reaction zone may preferably be comprised of one or more honeycomb monoliths. Preferred honeycomb monoliths are structures that comprise many (e.g., a plurality, meaning more than one) gas flow passages or conduits, arranged in parallel fashion with walls serving to separate each passage or conduit. Such reactor bed can include a single monolith or a plurality of monoliths disposed directly adjacent to each other. Each monolith can be formed by extruding or die pressing monolith blocks with shaped (e.g., square or hexagonal) cross-section and two- or three-dimensionally stacking, such blocks above, behind, and beside each other. Monoliths are particularly effective as reactor beds because they provide high heat transfer capacity with minimum pressure drop.

Each monolith provides at least one passage (e.g., flow path) for respective streams used in the present techniques. Honeycomb monoliths can be further characterized as having open frontal area (or geometric void volume), such as from 20% to 80%, and having conduit density, such as from 50 to 2000 pores per square inch (pores/in$^2$), more preferably from 50 to 500 pores/in$^2$. The conduits may have a diameter of only a few millimeters, and preferably in the range of 0.5 millimeters (mm) to 10 mm.

Higher concentrations of ethylene may be produced from the pyrolysis reactor by injecting the reactive feed into an open flow path volume at the second end of the pyrolysis reactor into the secondary reaction zone. The reactive feed is mixed with the primary pyrolysis product that emerges from the bed packing, and pyrolysis of hydrocarbon in the reactive feed is carried out, along with unreacted hydrocarbon in the primary pyrolysis product, to produce the secondary pyrolysis product.

Pyrolysis of hydrocarbon in the reactive feed in the secondary reaction zone produces unsaturated hydrocarbon, such as ethylene. In a particular embodiment, the secondary pyrolysis conditions in the secondary reaction zone are such that higher quantities of ethylene are present in the secondary pyrolysis product relative to ethylene present in the primary pyrolysis product. For example, pyrolysis temperature, or peak pyrolysis gas temperature, of the secondary pyrolysis reaction in the secondary reaction zone is less than the peak pyrolysis temperature in the primary reaction zone.

The peak pyrolysis gas temperature of the secondary pyrolysis reaction in the secondary reaction zone can be at least 100° C., or at least 200° C., or at least 500° C. less than the peak pyrolysis gas temperature in the primary reaction zone. The peak pyrolysis gas temperature of the secondary pyrolysis reaction in the secondary reaction zone is, however, preferably at least 600° C., or more preferably at least 700° C. Accordingly, the secondary pyrolysis reaction may involve exposing streams to temperatures in the range from 600° C. to 1800° C., 600° C. to 1300° C., in the range from 700° C. to 1200° C., in the range from 800° C. to 1100° C., or in the range from 850° C. to 1050° C.

The residence time in the secondary reaction zone may also be relatively short, yet long enough to allow sufficient mixing of the reactive feed with the primary pyrolysis product. In one embodiment, the residence time in the secondary reaction zone is at least 0.05 seconds, preferably at least 0.1 seconds. Preferably, the residence time in the secondary reaction zone is ≤5 seconds, more preferably ≤2 seconds.

The amount of reactive feed injected into the reactor is not greater than that of the pyrolysis feed based on the mass of the hydrocarbon in the reactive feed and pyrolysis feed (e.g., on a hydrocarbon only basis). In one embodiment, the reactive feed is injected into the secondary reaction zone of the pyrolysis reactor and the pyrolysis feed is injected into the primary reaction zone at a respective mass flow ratio in the range of 0.5:1 to 2.0:1, of 0.5:1 to 0.9:1, or of 1:1 to 2:1, based on the mass of the hydrocarbon in the reactive feed and pyrolysis feed.

The reactive feed can be heated prior to entering the secondary reaction zone. For example, the reactive feed can be heated to a temperature of at least 200° C. or at least 300° C. prior to entering the secondary reaction zone. It is desirable, however, to heat the reactive feed to a temperature of ≤600° C., preferably ≤500° C., more preferably ≤400° C., to avoid excessive pyrolysis prior to entering the secondary reaction zone and to provide more sensible cooling when mixed with the pyrolysis product stream.

III. Heating Step

To carry out the pyrolysis reactions in both the primary and secondary reaction zones, the bed packing in the primary reaction zone is heated in the heating step. To heat the bed packing, combustion feeds (which may be referred to as combustion streams along the flow path) are supplied to or injected into the reactor so that combustion is initiated in the mixing zone of the reactor. The combustion feeds can be supplied to the mixing zone directly through the second end of the pyrolysis reactor or indirectly though the first end of the pyrolysis reactor by way of conduits or passages that bypass the channels utilized to remove the combustion products from the reactor. That is, one or more combustion streams flow into the mixing zone, where combustion is initiated. The combustion streams may also flow through conduits through a combustion preheat zone and then into the mixing zone.

The combustion streams mix together and exothermically react, initially reacting in the mixing zone to produce heat. The flow of the combustion streams continues into the bed packing, carrying along the exothermic heat of reaction, thereby heating the bed packing in the primary reaction zone. The combustion streams may include a fuel stream and an oxidant stream that are maintained substantially separate until passing to the mixing zone. These streams are capable of reacting together and combusting to supply or generate heat and produce combustion products.

The combustion streams may include two or more individual feeds or reactants that are to be combined to form a combustion reaction or a mixture of the two or more feeds, such as a fuel that does not contain oxidants (e.g., $O_2$) or non-combustible non-volatiles and a combustion oxidant that may include an oxygen or oxygen containing fluid. The fuel stream may be a hydrogen-containing composition of hydrogen, hydrocarbon or a mixture thereof Exothermically reacting the fuel and oxidant provides at least a portion of the heat utilized by the pyrolysis, e.g., ≥50%, such as ≥75%, or ≥95% of the heat utilized by the primary pyrolysis reaction. Additional heat, when needed, can be provided to the regenerative, reverse-flow pyrolysis reactor by, e.g., a burner or furnace, e.g., a furnace external to the reactor, but in thermal communication therewith.

In certain embodiment, the fuel can comprise, e.g., molecular hydrogen, synthesis gas (mixtures of CO and $H_2$), or hydrocarbon, such as ≥10.0 wt % hydrocarbon (including mixtures thereof), or ≥50.0 wt % hydrocarbon, or ≥90.0 wt % hydrocarbon based on the weight of the fuel. When the fuel comprises hydrocarbon, the particular hydrocarbon selected is not critical. For example, in an embodiment, the hydrocarbon comprises one or more of the hydrocarbons specified for the pyrolysis feed, e.g., methane. In an embodiment, the hydrocarbon is derived from, comprises, consists essentially of, or consists of one or more of methane, methane containing streams such as coal bed methane, biogas, associated gas, natural gas, and mixtures or components thereof, etc. When the fuel comprises hydrogen and/or hydrocarbon, the choice of oxidant is not critical, provided the oxidant is capable of exothermically reacting with the hydrogen and/or hydrocarbon. For example, in an embodiment, the oxidant comprises, e.g., molecular oxygen and/or ozone.

The oxidant stream may include an oxygen composition that has sufficient oxygen content to enable the fuel to combust. Oxidant can be supplied in any form suitable for combustion, such as pure oxygen or in the form of air. The oxidant stream may include, but is not limited to, air, oxygen or mixtures thereof. For example, the oxidant can comprise, e.g., ≥10.0 wt % molecular oxygen, e.g., ≥50.0 wt % molecular oxygen, or ≥90.0 wt % molecular oxygen based on the weight of the oxidant. Any of the fuel or oxidant may additionally include non-combustible compounds or diluents, such as $N_2$, $CO_2$, $H_2O$, and/or other inert gases.

In an embodiment, the combustion oxidant comprises oxygen in an amount of at least 80% of stoichiometric for complete combustion of the combustion fuel composition. Preferably, the combustion oxidant comprises molecular oxygen in a stoichiometric amount for complete combustion, and more preferably in an amount in excess of stoichiometric for complete combustion of the combustion fuel composition in the combustion streams.

The fuel and the oxidant are preferably not mixed until entering the mixing zone. That is, the combustion streams are flowed to the mixing zone, optionally through a combustion preheat zone, in separate channels. The combustion preheat zone may include one or more channels disposed around the bed packing to recover a portion of the heat produced in the process and/or may include an indirect heat exchanger configured to pass the combustion products on one side of the heat exchanger and feed on the other side of the heat exchanger.

The combustion products are flowed into the bed packing within the primary reaction zone with the heat of combustion being absorbed by the bed packing. This absorbed heat by the bed packing is sufficient to enable pyrolysis of the hydrocarbon in the pyrolysis stream. The combustion heat may also be sufficient to remove coke or tar components that may have accumulated in the primary reaction zone during a previous pyrolysis step via burning, thereby regenerating the primary reaction zone. Also, the reverse flow may be utilized to remove non-volatiles that have accumulated within the reactor. This heating and regeneration of the heating step is particularly beneficial in a cyclic process that incorporates both the heating step and the pyrolysis step.

IV. Pyrolysis Step

In the primary reaction zone, pyrolysis feed comprising hydrocarbon, and optionally diluent, such as molecular hydrogen ($H_2$), is supplied to or injected into the primary reaction zone via pyrolysis injection components. The pyrolysis feed may be supplied to or injected into the primary reaction zone following the removal of the combustion products from the heating step, which may include a sweeping or purging step to remove products from the internal regions of the entire reactor, and is flowed through the channels of the bed packing in the primary reaction zone to a first end of the reactor. The direction of flow of the pyrolysis stream through the flow channels of the pyrolysis zone may be counter to the direction of flow of the combustion streams, or in certain embodiments may be in the same direction, which may also involve some alternating patterns of flow.

As the pyrolysis stream flows through the channels of the bed packing, the temperature along the path of flow increases. As the temperature increases to the appropriate level, pyrolysis of the hydrocarbon in the pyrolysis stream takes place in the primary reaction zone. Following the bed packing, the primary pyrolysis product (e.g., unreacted and reacted hydrocarbons from the bed packing) flows into the secondary reaction zone, and mixes with the quench fluid, such as a reactive feed that contains a second hydrocarbon. The reactive quench or second pyrolysis reaction is carried out under the conditions described above. This secondary pyrolysis reaction serves to cool the components of the primary pyrolysis product and to further pyrolyze hydrocarbons of the first and second hydrocarbons contained in the mixture of gases in the secondary reaction zone. The resulting reactions produce the secondary pyrolysis product having a higher concentration of ethylene as compared to the primary pyrolysis product. The secondary pyrolysis product is then conducted away from the pyrolysis reactor, optionally passed to a quenching zone for further cooling, and further passed for processing in recovery units to process and separate one or more of acetylene, ethylene, and hydrogen.

In the pyrolysis reactor, both the primary and secondary pyrolysis reactions are carried out relatively quickly to avoid over-cracking so as to avoid excessive formation of undesirable by-products, particularly coke and tar compositions. Accordingly, pyrolysis reactors may be characterized in terms of the residence time of pyrolysis gases in the reactor. Residence time is considered to be the total time from the hydrocarbons entry into the pyrolysis reactor and the corresponding exit of the pyrolysis product from the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present techniques, residence time (in either form) may be approximated using interpolation and extrapolation of discreet composition and temperature measurements and/or using model-based estimations of temperature and composition, as is known in the art. As an example, the residence time for a reverse-flow regenerative reactor is the time from the exit of the pyrolysis feed injection component to the primary reaction zone, time traveling through the primary and secondary reaction zones and the time to exit the pyrolysis reactor. Residence times for this pathway may be ≤0.5 second, ≤0.3 second, and preferably ≤about 50 milliseconds, or in the range of 0.001 to 1.0 seconds, or in the range of 0.5 seconds to 0.001 seconds.

V. Pyrolysis Feed

"Pyrolysis feed" refers to the feed that is fed directly to (i.e., enters) the primary reaction zone. The pyrolysis feed can be derived from any suitable hydrocarbon feed, in which the hydrocarbon feed may be optionally treated to provide the pyrolysis feed, such that the pyrolysis feed can comprise any variety of hydrocarbon compounds. For example, a hydrocarbon feed may include substantial amounts of non-volatiles such that the hydrocarbon feed is not be desirable as pyrolysis feed, unless at least a portion of the non-volatiles are removed. In such cases, the hydrocarbon feed can be treated to reduce extremely high quantities of non-volatiles or any other type of hydrocarbon or non-hydrocarbon component as desired. Examples of such treatment include, but are not limited to, treatment by resid hydrotreaters, hydrovisbreakers, acid washes, filtration, chelation, membrane or filtration, resid hydrotreater, acid extraction, or any number of metals reduction processes.

As used herein, the "hydrocarbon feed" can refer to hydrocarbon in either the pyrolysis feed or reactive feed, which is discussed further below. These hydrocarbons (compounds having C bound to H) may contain (i) minor components of heteroatoms (less than (<) 10 weight percent (wt %)) covalently bound to hydrocarbons and (ii) minor components of heteroatoms (<10 wt %) not bound to hydrocarbons (e.g., $H_2O$), wherein these weight percents are based on the weight of the hydrocarbon feed. Reference to "hydrocarbon compounds" or "hydrocarbons in the hydrocarbon feed" or "hydrocarbons of the hydrocarbon feed" or "hydrocarbons of the pyrolysis feed" also refers to molecules that contain at least hydrogen and carbon, and contain heteroatoms such as oxygen, sulfur, and nitrogen. Weight percents of hydrogen and carbon, as used to characterize the hydrocarbon content of the feed, are typically provided as a percent of the hydrocarbons in the feed. Preferably, the hydrocarbon compounds are comprised of at least 75 percent (%) of both carbon and hydrogen, based on total atom content of the hydrocarbon.

In an embodiment, the hydrocarbon is derived from one or more source materials. The term "source materials" means sources, containers, conduits, vessels, reservoirs, etc., of hydrocarbon. Examples of hydrocarbon include one or more of methane, methane-containing streams, distillates, residues, hydrocarbon streams derived from plant or animal matter and/or combinations thereof. Suitable hydrocarbon source materials include those described in U.S. Pat. Nos. 7,943,808 and 7,544,852, which are incorporated by reference herein in their entirety.

Particular hydrocarbons useful according to this invention in both the primary and secondary pyrolysis reactions are those that can be pyrolyzed to produce a product containing acetylene containing compounds, ethylene containing compounds or both. Particularly preferred are hydrocarbon compounds that can be pyrolyzed to produce product containing equal to or greater than (≥) 1 volume percent (vol. %), more preferably ≥3 vol. %, and most preferably ≥6 vol. % acetylene containing compounds, based on total volume of pyrolyzed product produced form the pyrolysis process.

The pyrolysis feed is the hydrocarbon-containing stream provided to the primary reaction zone (e.g., the stream that enters the pyrolysis reactor) and may contain one or more hydrocarbon feeds as well as one or more diluents such as molecular hydrogen ($H_2$). The pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2$/C) may be from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of the pyrolysis feed may result in a total atomic ratio of hydrogen (H) to carbon (C) in the pyrolysis feed that is in the range of 0.1 to 20 or in the range of 3 to 15. The weight percent of total hydrogen in the pyrolysis feed may be greater than that in the hydrocarbon feed that it is derived from. For example, the weight percent of total hydrogen in the pyrolysis feed may be from 8 wt % to 54 wt %.

The term "hydrogen content" means atomic hydrogen bound to carbon and/or heteroatoms covalently bound thereto and which excludes molecular hydrogen ($H_2$) in feed expressed as a weight percent based on the weight of the hydrocarbons in the feed. Hydrogen content as applied to pyrolysis feed is expressed as an ASTM weight percent of hydrocarbons in the respective feed. As used herein, the expression "low hydrogen content feed" or "low hydrogen content hydrocarbon feed" means a feed with a hydrogen content of less than or equal to (≤) about 14 wt %. The hydrogen content of feeds, reactants and products for present purposes can be measured using any suitable protocol (e.g., ASTM D4808-01 (2006), Standard Test Methods for Hydrogen Content of Light Distillates, Middle Distillates, Gas Oils, and Residua by Low-Resolution Nuclear Magnetic Resonance Spectroscopy or ASTM D5291-10 Standard Test Methods for Instrumental Determination of Carbon, Hydrogen, and Nitrogen in Petroleum Products and Lubricants).

To minimize undesirable quantities of carbon oxides (e.g., CO, $CO_2$) in the pyrolysis product and to maximize the ethylene and/or acetylene content of the pyrolysis products, the pyrolysis feed is low in molecular oxygen ($O_2$) content and/or low in water ($H_2O$) content. By lessening undesired components, undesirable combustion reactions in primary and/or secondary reaction zones may be reduced. Preferably, the pyrolysis feed is comprised of ≤10 mole % $O_2$, alternatively ≤5 mole % $O_2$, or alternatively ≤2 mole % $O_2$, based on total amount of pyrolysis feed entering the primary reaction zone. Also, the pyrolysis feed may preferably comprise ≤10 wt % $H_2O$, or ≤5 wt % $H_2O$, 2 wt % $H_2O$, based on total weight of the pyrolysis feed. As an example, the pyrolysis feed may include >50 wt %, >70 wt %, >90 wt % methane, based on total weight of the pyrolysis feed.

VI. Reactive Feed

The reactive feed comprises hydrocarbon, which may include those described above in the pyrolysis feed. The reactive feed can comprise hydrocarbon that is the same or different from the hydrocarbon in the pyrolysis feed and in the same proportions. The reactive feed can also include water, molecular oxygen or both, as long as amount of water and molecular oxygen are within the limits as describe above in the pyrolysis feed. The relative conditions for pyrolyzing the hydrocarbon in the secondary reaction zone are also described above.

The reactive feed may not include substantial amounts of inert compounds. Inert compounds are considered substantially unreactive with the hydrocarbon in the pyrolysis reaction. Examples of useful diluents include, but are not limited to, hydrogen, nitrogen, water, and the noble gases, such as helium, neon, and argon. For example, the reactive feed can comprise ≤20 wt %, alternatively ≤10 wt %, alternatively ≤5 wt %, of diluents, based on total weight of the reactive feed stream entering the secondary reaction zone.

To minimize undesirable quantities of carbon oxides (i.e., $CO$, $CO_2$) in the secondary pyrolysis product, which can occur due to undesirable combustion reactions in the secondary reaction zone, the reactive feed is low in molecular oxygen ($O_2$) content. Preferably, the reactive feed is comprised of ≤10 mole % $O_2$, alternatively ≤5 mole % $O_2$, or alternatively ≤2 mole % $O_2$, based on total amount of reactive feed entering the secondary reaction zone.

As noted above, the reactive feed comprising hydrocarbon may be injected at the second end of the reactor, such that the reactive feed is mixed with the primary pyrolysis product that emerges from the bed packing and at a location downstream of the bed packing. The secondary reaction zone may include an open flow path volume such that the primary pyrolysis product from the primary reaction zone and the reactive feed are sufficiently mixed and pyrolysis of hydrocarbon in the mixed stream is carried out. The mixing of the reactive feed and the primary pyrolysis product may be enhanced within the open flow path volume via the use of a distribution/mixing device and/or other suitable mixing mechanism.

The reactive feed may be utilized to quench the primary pyrolysis product and/or to convert the hydrocarbons in the reactive feed along with components, such as unreacted hydrocarbons, in the primary pyrolysis product into secondary pyrolysis products in the secondary reaction zone. That is, the reactive feed may be provided at a temperature below the temperature of the primary pyrolysis product to cool the primary pyrolysis product from the primary reaction zone. As an additional enhancement, the reactive feed may continue pyrolysis of unreacted and/or additional hydrocarbons in the reactive feed.

To manage the temperature for the reactions of the reactive feed and primary pyrolysis product, the reactive feed may be introduced at a location downstream of the bed packing where the peak pyrolysis gas temperature is sufficient to convert the hydrocarbons in the reactive feed. This may involve passing the primary pyrolysis product through a predetermined distance, indirect quenching the primary pyrolysis product through a heat exchange zone, and/or combining a quench fluid (e.g., reactive feed or non-reactive feed) with the primary pyrolysis product downstream of the bed packing and upstream of the reactive feed.

As an example, the reactive feed may include >50 wt %, >70 wt %, >90 wt % ethane, based on total weight of the reactive feed. Further, the reactive feed may be provided to the reactor at a temperature ≤600° C., ≤500° C., ≤300° C., or ≤200° C.

The heating step involves mixing a fuel stream with the main oxidizing stream flowing in one direction, while the quench step involves mixing a quench stream (either reactive or non-reactive) with the pyrolysis product stream flowing the other direction. A distribution device may be advantageously utilized for both purposes, that is, to mix the fuel with oxidant during the heating step, and to also mix the quench stream with the pyrolysis product stream during the pyrolysis step.

VII. Final Pyrolysis Product

The products that are produced in both the primary pyrolysis reactions and secondary pyrolysis reactions comprise ethylene compounds and acetylene compounds. The secondary pyrolysis product, however, has a greater ratio of ethylene to acetylene (e.g., alkene to alkyne) than the primary pyrolysis product. For example, the secondary pyrolysis product can be comprised of ethylene and acetylene at a respective mass ratio of ≥1.1:1, or ≥1.5:1, or ≥2:1 based on the weight percentage of ethylene and acetylene in the secondary pyrolysis product.

The secondary pyrolysis product can include non-alkyne and non-alkene compounds, but in limited amounts. Preferably, the secondary pyrolysis product includes ≤50 wt % non-alkyne and non-alkene compounds, alternatively 40 wt % non-alkyne and non-alkene compounds, alternatively 30 wt % non-alkyne and non-alkene compounds, based on total weight of the secondary pyrolysis product as it emerges from the pyrolysis reactor. Further, the unsaturated hydrocarbon in the secondary pyrolysis product is comprised of at least 20 wt %, or at least 30 wt % ethylene compounds, based on total weight of the unsaturated hydrocarbon.

VIII. Cooling the Secondary Pyrolysis Product

The secondary pyrolysis product can be removed from the second end of the pyrolysis reactor and cooled by any appropriate means. For example, the reactor effluent, which includes at least a portion of the secondary pyrolysis product, can be cooled by heat exchange with a heat exchange medium. In one embodiment, heat exchange is accomplished by flowing the reactor effluent through a heat exchanger in which heat is exchanged with a heat exchange fluid that also flows through the heat exchanger. Examples of heat exchange fluid include, but are not limited to, gases or liquids, such as any variety of oils or water. In one embodiment, the heat exchange fluid is water, with the water absorbing sufficient heat from the effluent product to produce steam.

Optionally, the reactor effluent can also be cooled by direct contact with a liquid quench medium that is capable of removing heat from the secondary pyrolysis product and/or the reactor effluent, with little to no chemical reactions taking place. For example, the quench medium can be water or quench oil. If the liquid quench medium is water, the water can contact the reactor effluent with the effluent being is cooled through vaporization of the water, thus producing steam. The steam can then be used for heat recovery in a subsequent operation. If the liquid quench medium is a hydrocarbon liquid, such as a quench oil, then the quench oil can contact the reactor effluent, thus producing a heated quench oil. The heated quench oil can then be used for heat recovery in a subsequent operation.

In one embodiment, the secondary pyrolysis product is removed from the second end of the pyrolysis reactor and contacted with a liquid quench medium. This mixture of secondary pyrolysis product and liquid quench medium is then flowed through a heat exchanger. Contact with the liquid quench medium can also be carried after flowing the secondary pyrolysis product through the heat exchanger.

IX. Coke Removal

At least a portion of the combustion streams can be optionally used as a decoking source to remove coke by-products from one or more effluent lines from the pyrolysis reactor. For example, as noted above, regenerative reverse-flow reactors include a heating step (e.g., involving heating and regenerating) and a pyrolysis step. In the heating step, a hydrocarbon or hydrogen-containing stream and an oxygen-containing stream are combusted in the mixing zone to produce heat for the pyrolysis step. The combustion products are typically removed from the reactor via the combustion effluent line. However, as a decoking process, the combustion products and/or additional oxygen may be flowed along the flow path of the pyrolysis product to decoke the lines and equipment downstream of the reactor. Excess oxygen that is present in the combustion product can combust hydrocarbons present in the effluent, burning off coke that may be present and the resulting combustion products may be diverted via valves and lines into the combustion effluent line.

X. Examples

FIG. 1 is a simplified schematic diagram of one embodiment of the pyrolysis process in which the pyrolysis reaction is carried out in a regenerative reverse-flow reactor. The reactor 100 has a housing that encloses an interior region, which may include various valves and conduits to pass streams between the interior region and locations external to the interior region. For instance, an oxidant and fuel are input into a first end 102 of the pyrolysis reactor 100. The oxidant and fuel provided via lines 103a and 103b flow through respective channels 104a and 104b and enter a mixing zone 106, where the oxidant and fuel are mixed and combustion is initiated, thereby releasing heat. Any unreacted oxidant and fuel are further mixed as they flow through one or more mixing components 108 and into the bed packing 120 where combustion is continued. The mixing components 108 may include baffles, plates and/or other tortuous paths to intermingle the flow of different streams. During the heating step, sufficient heat is absorbed in the material of the bed packing 120 from the combustion process to maintain the desired temperature (e.g., the peak pyrolysis gas temperature) for pyrolysis in the bed packing 120 during the pyrolysis step. The desired temperature for pyrolysis is typically a higher temperature than desired peak pyrolysis gas temperature within the reactor. Combustion products are removed from the reactor via a line 112.

Following the heating step, the pyrolysis feed is introduced into the bed packing 120 via a distributor 118 and line 114. The distributor 118 separates the pyrolysis stream into the different passages of the bed packing 120. Heat is absorbed from the bed packing 120 by the pyrolysis stream, and the primary pyrolysis reaction is carried out producing a primary pyrolysis product. The bed packing 120 may be a monolith, pebble bed, or other suitable bed packing material with multiple passages through the material.

The primary pyrolysis product leaves the bed packing 120 and passes through the mixing component 108, flowing through the mixing zone 106 toward the secondary reaction zone 111. A reactive feed, such as an ethane containing stream, is provided via line 123 and combined with the primary pyrolysis product passing through the secondary reaction zone 111 via a reactive feed distribution device 122. This mixture of these streams results in a secondary pyrolysis reaction that is carried out as the streams interact with each other to produce a secondary pyrolysis product. The reactive feed distribution device 122 may include a mixing unit, a sparger, or conduit with valves and/or nozzles, or other suitable devices.

The secondary pyrolysis product may optionally be further cooled or quenched by contacting the secondary pyrolysis product with a non-reactive quench feed, which may include a liquid quench medium, such as a liquid water stream and/or quench oil stream, provided via line 125 downstream of the secondary reaction zone 111 via a liquid quench distributor 124. The liquid quench distributor 124 may include a mixing unit, a sparger or conduit with valves and/or nozzles, or other suitable devices. The liquid quench medium may further cool the secondary pyrolysis product to a temperature of ≤500° C. or ≤300° C.

In this embodiment 100, the reaction zones may be understood with reference to flow path of the pyrolysis stream. The primary reaction zone 110 may include the distributor 118, the bed packing 120 and overlap with the mixing zone 106, while the mixing zone 106 may include the mixing components 108 and the volume (e.g., open void space) between the mixer 108 and the reactive feed distribution device 122. The secondary reaction zone 111 may include the volume from the reactive feed distribution device 122 to the liquid quench distributor 124, while the quenching zone may include the volume from the liquid quench distributor 124 to the exit of the reactor or a location downstream of the reactor.

In an alternative embodiment, a quenching fluid may be combined with the primary pyrolysis product upstream of the introduction of the reactive feed. The quenching fluid may be utilized to manage the temperature of the second reaction zone to be within a preferred temperature range. In this embodiment, the secondary reaction zone, quench zone and mixing zone may be adjusted, while the primary reaction zone 110 remains the same. The mixing zone 106 may include the mixing components 108 and the volume (e.g., open void space) between the mixer 108 and the reactive feed distribution device 122, which may overlap with the a quenching zone between from liquid quench distributor 124 to the reactive feed distribution device 122. The secondary reaction zone 111 may include the volume from the reactive feed distribution device 122 to a subsequent quenching step or the volume from the reactive feed distribution device 122 to the exit of the reactor.

Beneficially, this configuration provides a less complex design compared to other systems, but relies upon active quenching to manage the cooling of the pyrolysis products. That is, the use of quench fluids, such as the reactive feed and the liquid quench medium, are utilized to adjust the temperature profile of the stream through the reactor. In this manner, the product may be cooled at various locations to manage the pyrolysis product and lessen over cracking of the pyrolysis products.

Figure 2:
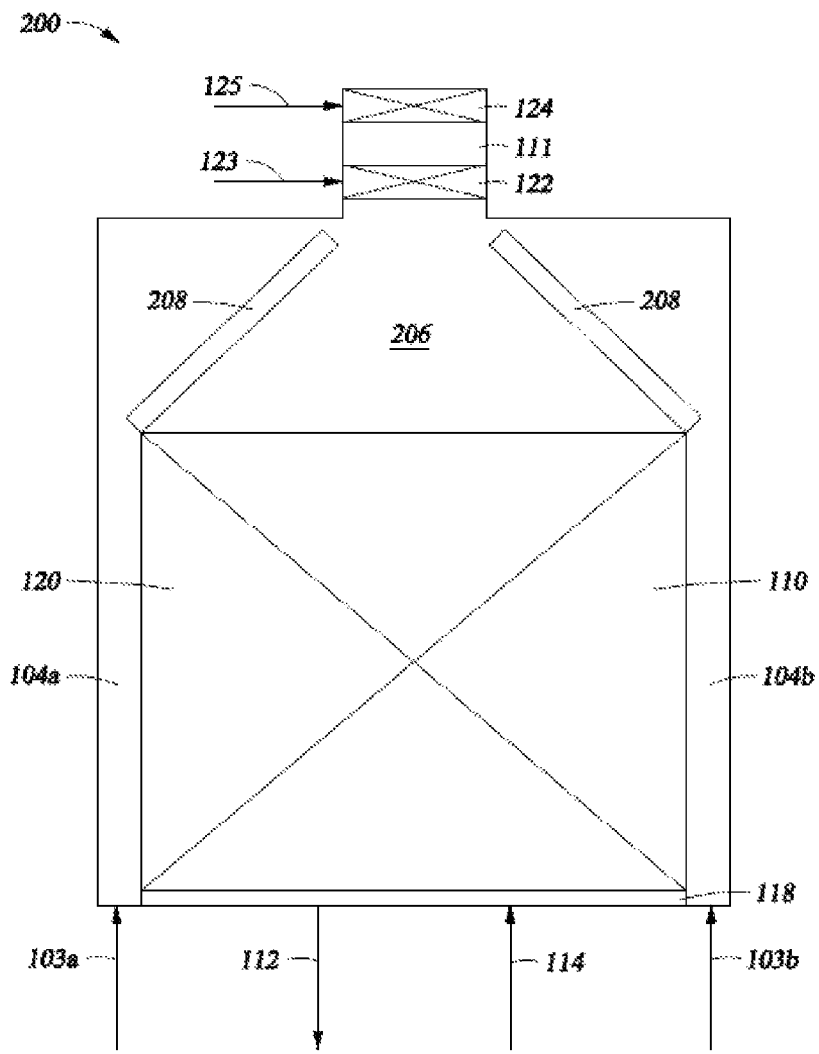
FIG. 2 is another simplified schematic diagram of an exemplary regenerative reverse-flow reactor having a different mixing component that the embodiment of FIG. 1.

FIG. 2 is another simplified schematic diagram of an exemplary regenerative reverse-flow reactor 200 including a different configuration for the mixing components 208 in the mixing zone 206. Components in this embodiment that are similar to those of FIG. 1 may use the same reference numerals for simplicity. In this embodiment 200, the one or more mixing components 208 are disposed within the interior region of the housing and along the flow path between the channels 104a and 104b for the oxidant and fuel and the mixing zone 206, but do not impede the flow path of the pyrolysis products from the bed packing 120. The mixing components 208 may include baffles, plates and/or other tortuous paths to intermingle the flow of different streams (e.g., oxidant and fuel) as it is provided to the mixing zone 206.

The heating step and pyrolysis step may be performed in a similar manner to that described in FIG. 1. However, in this configuration, fuel and oxidant are mixed as they pass through the mixing component 208. The mixing component 208 is utilized to distribute the fuel and oxidant streams into the mixing zone to provide a more uniform distribution of these streams to enhance the combustion reactions in a distributed manner through the mixing zone 206. This reaction, which releases heat, is then passed to through the passages in the bed packing 120, as discussed above.

During the pyrolysis step, the pyrolysis feed is introduced into the bed packing in a similar manner. However, the primary pyrolysis product may not pass through the mixing components 208, which may reduce the pressure drop associated with this component for the pyrolysis stream. As a result, the pyrolysis stream may pass through the reactor in a more efficient manner.

Figure 3A:
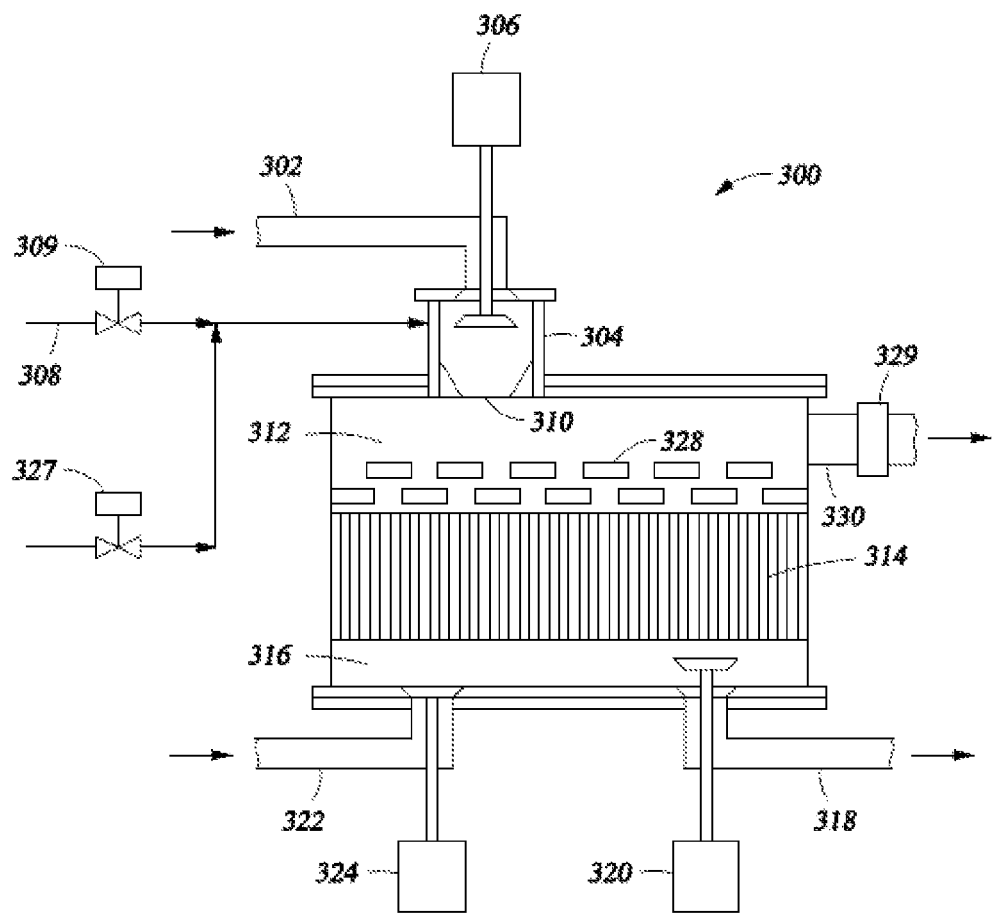
FIGS. 3A and 3B are additional simplified schematic diagrams of other exemplary embodiments of a regenerative reverse-flow reactor that can be used according to the present techniques.
Figure 3B:
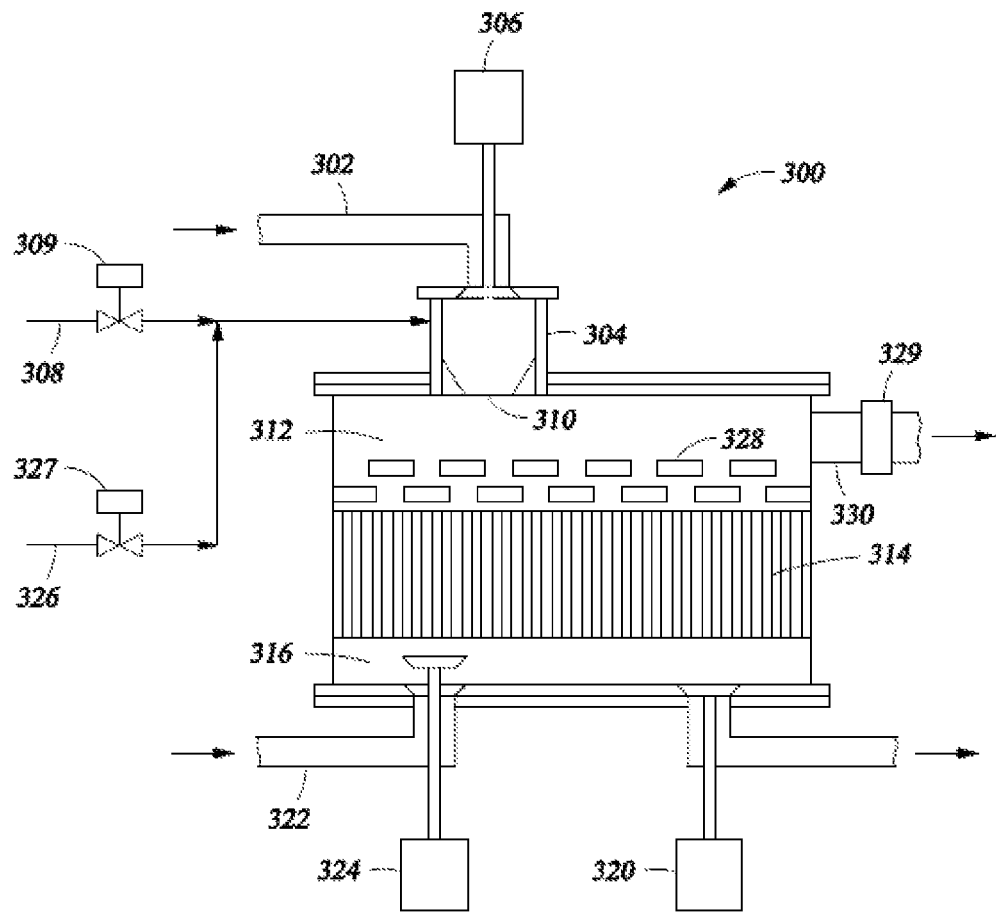

FIGS. 3A and 3B are simplified schematic diagrams of another embodiment of the pyrolysis process in accordance with the present techniques in which the pyrolysis reaction is carried out in a regenerative reverse-flow reactor. FIG. 3A illustrates the heating step in which the reactor is heated and/or regeneration of the reactor is carried out. FIG. 3B illustrates the pyrolysis steps in which hydrocarbons in the pyrolysis feed and reactive feed are pyrolyzed to produce unsaturated hydrocarbon compounds. To manage the flow through the interior region of the reactor's housing, various valves 306, 309, 320, 324, 327, and 329 are utilized to control the streams. For example, in FIG. 3A, valves 306, 309, and 320 are in the open position to flow combustion streams (e.g., combustion reactants and combustion products) through the reactor 300, while the valves 324, 327, and 329 are in the closed position to restrict the flow of pyrolysis stream. In FIG. 3B, valves 306, 309, and 320 are in the closed position to restrict the flow of combustion streams (e.g., combustion reactants and combustion products) through the reactor 300, while the valves 324, 327, and 329 are in the open position to flow of pyrolysis streams (e.g., pyrolysis feed and pyrolysis products) through the reactor 300. FIGS. 3A and 3B are described further below.

In FIG. 3A, an oxygen-containing stream (preferably preheated to a temperature in the range of 400° C. to 700° C.) is injected into a pyrolysis reactor 300 via line 302. The oxygen-containing stream passes through a burner 304 via burner valve 306, which may be a poppet valve. In the burner 304, the oxygen-containing stream is contacted with a combustion fuel (preferably preheated to a temperature of from 200° C. to 500° C.) via line 308 and valve 309 to produce combustion products.

Combustion products are injected through a burner throat 310 into the mixing zone 312 at a second end of the pyrolysis reactor 300. The combustion products then flow through the baffles 328 and bed packing 314 into a first end 316 of the pyrolysis reactor 300 and exit the pyrolysis reactor through combustion effluent line 318 via valve 320, which may include a poppet valve, for example. The primary reaction zone includes the volume that includes the bed packing 314 and baffles 328 having flow passages through which combustion and pyrolysis streams flow, while the mixing zone may include the baffles 328. During the heating step, heat is absorbed in the material of the bed packing 314 from the combustion products that is sufficient to maintain the desired pyrolysis temperature in the bed packing 314 during the pyrolysis step.

In FIG. 3B, a pyrolysis feed containing a first hydrocarbon is injected into the first end 316 of the pyrolysis reactor 300 through a line 322 via a valve 324. The pyrolysis feed is flowed from the first end 316 of the pyrolysis reactor 300 through the bed packing 314, where pyrolysis of the hydrocarbons in the pyrolysis feed is carried out. Pyrolysis is carried out at the appropriate conditions to produce a primary pyrolysis product that is comprised of unsaturated hydrocarbon, with a substantial portion of the unsaturated hydrocarbon being alkyne compounds, such as acetylene.

Primary pyrolysis product emerges from the bed packing 314 into the mixing zone 312 of the pyrolysis reactor 300. The secondary reaction zone may be the volume of the reactor where the reactive feed mixes with the pyrolysis product. At the same time, a reactive feed may be injected into the mixing zone 312 of the pyrolysis reactor 300 through a line 326 via valve 327 and the burner 304. The mixing zone 312 of the pyrolysis reactor 300 serves as an open flow path volume in which the reactive feed is mixed with the primary pyrolysis product that emerges from the bed packing 314 and pyrolysis of hydrocarbons in the reactive feed is carried out. That is, the secondary reaction zone may overlap with the mixing zone 312 for this configuration, while the primary reaction zone may include the first end 316 and the bed packing 314. Mixing of components in the secondary reaction zone 312 can be further enhanced by including mixing components internal to the secondary reaction zone 312 of the pyrolysis reactor 300, such as by baffles 328. The secondary pyrolysis product that is produced contains a substantial quantity of unsaturated hydrocarbon, and is removed from the pyrolysis reactor 300 by way of pyrolysis effluent line 330 via valve 329.

In this embodiment, the burner 304 is utilized to provide combustion products and to provide the reactive feed. This burner 304 provides an isolated location that may manage the combustion reaction heat without directly damaging the bed packing 314. Also, the reactive feed may absorb some of the heat from the burner and utilize this heat to preheat the reactive feed upstream of the mixing with the pyrolysis product from the bed packing 314. Further, the baffles 328 may provide another protective device for the bed packing 314. That is the burner 304 and the baffles 328 may prolong the useful life of the bed packing 314.

Figure 4:
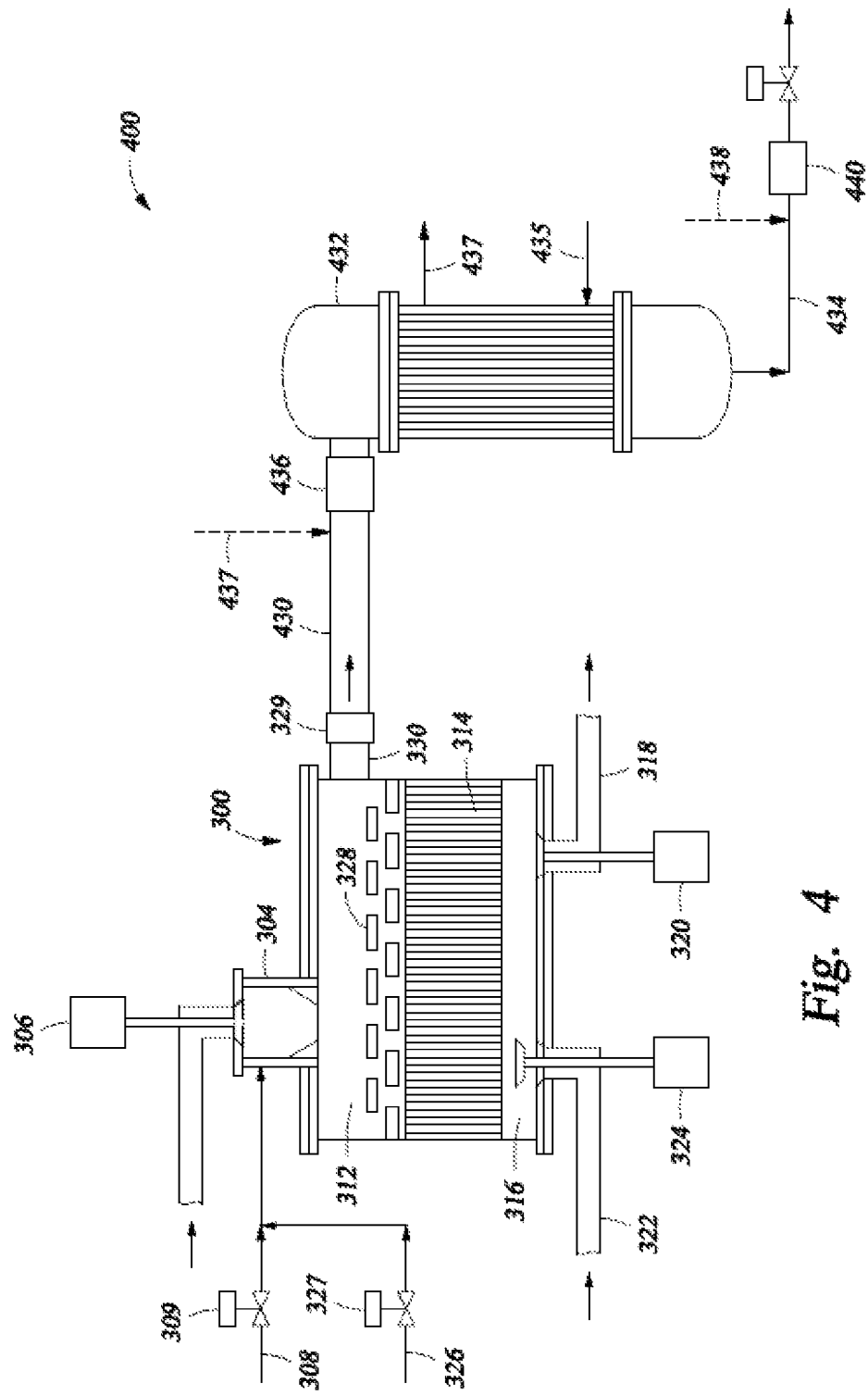
FIG. 4 is yet another exemplary embodiment of the thermal pyrolysis process in which the thermal pyrolysis reaction is carried out in a regenerative reverse-flow reactor, and the reactor effluent is cooled using a non-reactive quench oil and a heat exchanger.

FIG. 4 is yet another exemplary embodiment of the thermal pyrolysis process in accordance with the present techniques in which the thermal pyrolysis reaction is carried out in a regenerative reverse-flow reactor, and the reactor effluent is cooled using a quench medium, such as a non-reactive quench oil, and a heat exchanger 432. Components in this embodiment that are similar to those of FIG. 3B may use the same reference numerals for simplicity. This embodiment may provide additional quenching as described further below.

In FIG. 4, the pyrolysis streams may flow through the reactor 300 as noted above for FIG. 3B to form the secondary pyrolysis product. The secondary pyrolysis product may pass through valve 329 and flow through line 430 to a heat exchanger 432. Along the flow path to the heat exchanger 432, a quench fluid may optionally be injected into the line 430 via quench medium line 437 into a quench medium distributor 436. The quench medium distributor 436 may be located along the line 430 upstream of the heat exchanger 432. The quench medium distributor 436 may include one or more joints in the respective lines, one or more static mixers, one or more nozzles, one or more valves or other suitable equipment. The quench fluid may include quench oil, water and/or other suitable quenching fluid.

In this particular embodiment, the heat exchanger 432 may be utilized to further recover additional energy from the system. The heat exchanger 432 may include a shell and tube heat exchanger or other suitable indirect heat exchanger unit. Within the heat exchanger 432, a utility fluid may be provide via line 435 to provide indirect heat exchange with the effluent passing through the process conduits of the heat exchanger 432. The heated utility fluid may be removed from the heat exchanger 432 via line 437. In particular, the utility fluid may be water, which is utilized to produce steam, which can be used as a heat source for additional processing where desired.

To further cool the reactor effluent, a secondary optional quench medium may be injected into the line 434 downstream of the heat exchanger 432 via a secondary quench medium line 438 into a secondary quench medium distributor 440. Similar to the quench medium distributor 436, the secondary quench medium distributor 440 may include one or more joints in the respective lines, one or more static mixers, one or more nozzles, one or more valves or other suitable equipment. The quench fluid may include the same quench fluid utilized in line 437 or any of quench oil, water and/or other suitable quenching medium.

In one or more embodiments, the heat exchanger 432 may include one or more direct heat exchangers, indirect heat exchangers or a combination of both. Further, in yet another embodiment, the system may include a gas liquid separation unit upstream or downstream of the heat exchanger 432. The separation unit may be utilized to separate a vapor fraction from a bottoms fraction, which may contain liquids and any solids.

Figure 5:
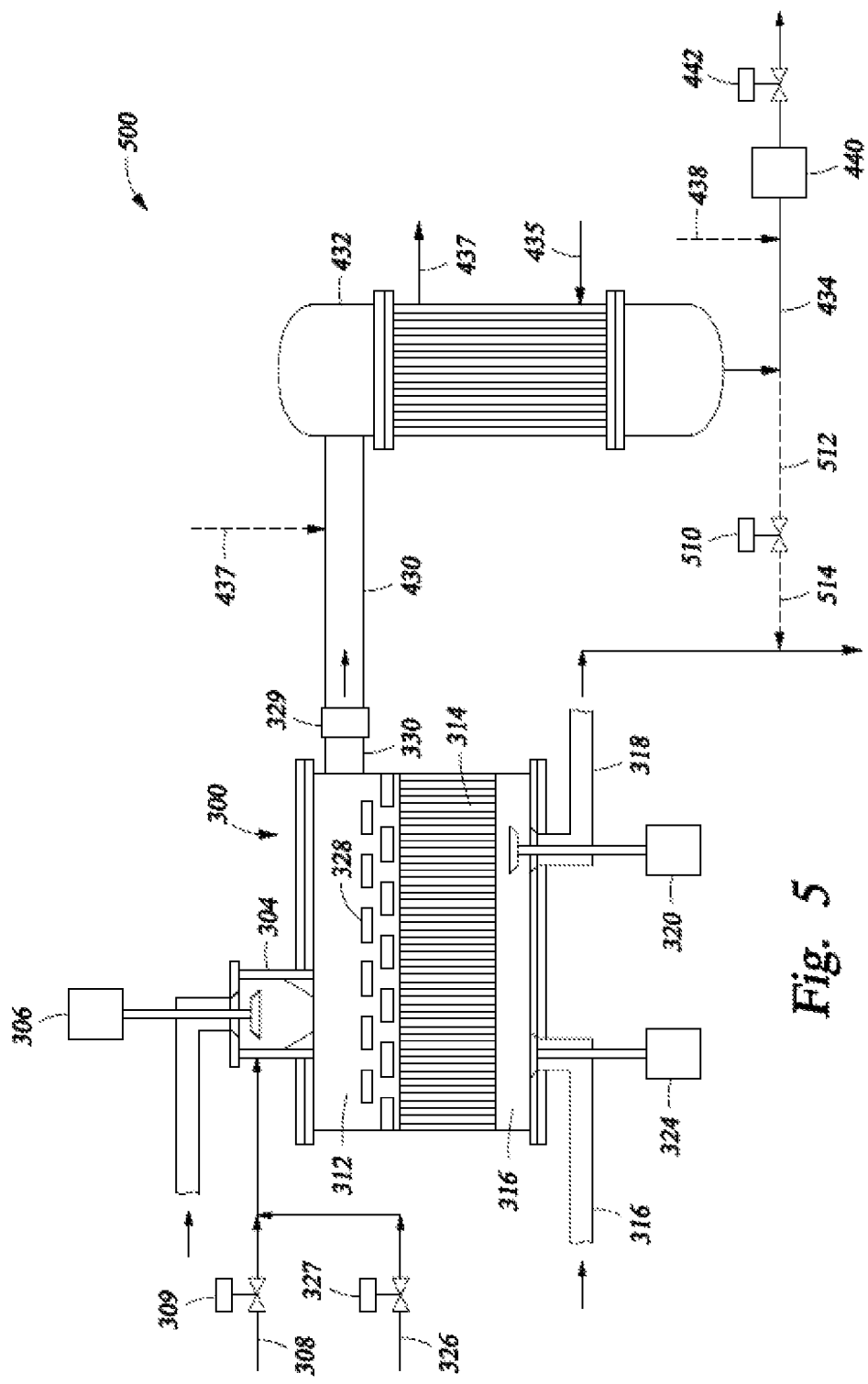
FIG. 5 is another exemplary embodiment of the thermal pyrolysis process in which the thermal pyrolysis reaction is performed in a regenerative reverse-flow reactor and in which at least a portion of the combustion stream is used to remove coke by-products in the system.

FIG. 5 is another exemplary embodiment of the thermal pyrolysis process in accordance with the present techniques in which the thermal pyrolysis reaction is performed in a regenerative reverse-flow reactor and in which at least a portion of the combustion stream is used to remove coke by-products in the system. Components in this embodiment that are similar to those of FIG. 4 may use the same reference numerals for simplicity. This embodiment may provide tar and coke removal mechanisms to further manage the process as described further below.

In this embodiment 500, the flow of combustion streams may be utilized to decoke the heat exchanger 432 and associated lines 330 and 430. To manage the combustion stream, valves 306, 309, 320, 329, and 510 are in the open position to flow combustion streams (e.g., combustion reactants and combustion products) through the reactor 300 and heat exchanger 432, while the valves 324, 327, and 442 are in the closed position to restrict the flow of combustion stream through these conduits. By passing the combustion stream through the heat exchanger 432, the coke and/or other fouling buildup within the heat exchanger may be burned off and/or moved by the velocity of the stream flowing through the conduits. Once it is determined that sufficient coke has been removed, the normal hydrocarbon processing mode may be resumed.

Figure 6:
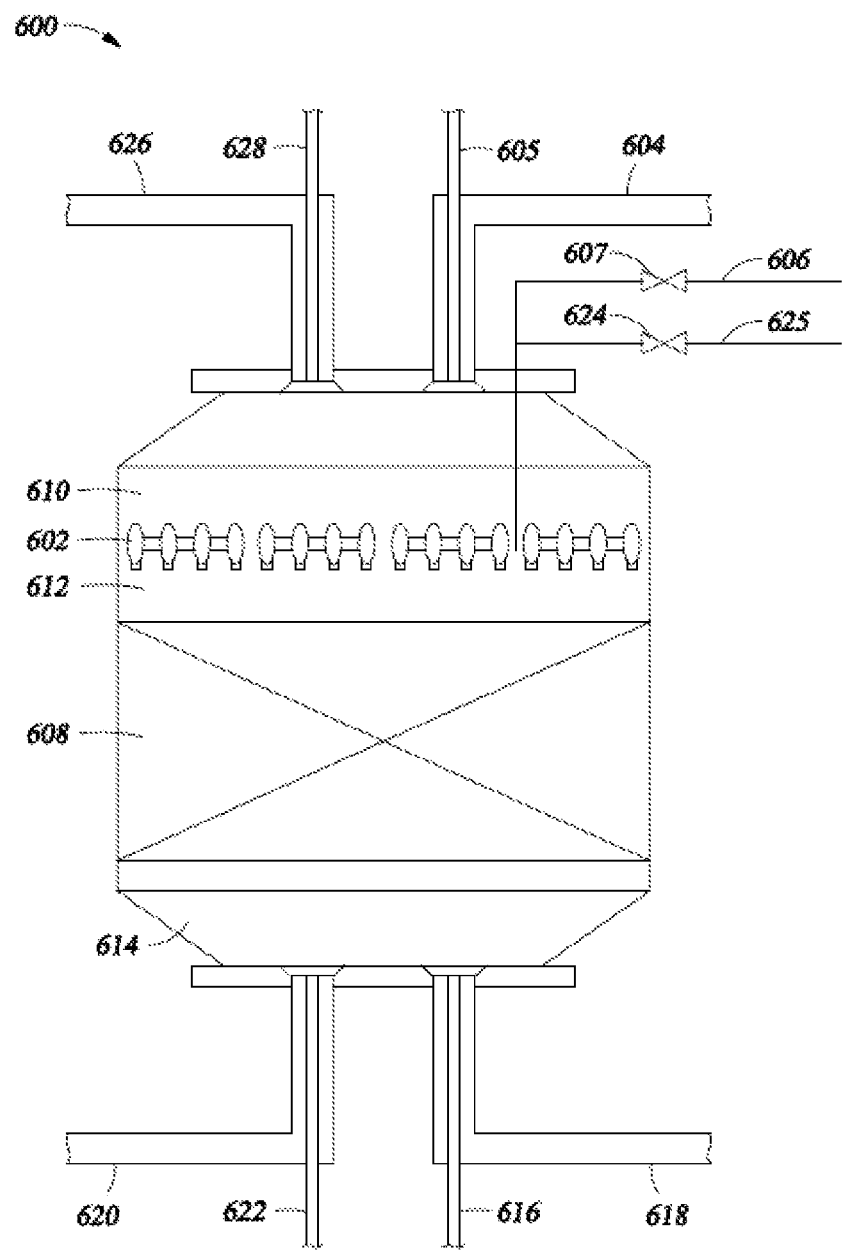
FIG. 6 is yet another schematic diagram of an exemplary embodiment of a thermal pyrolysis process in which the thermal pyrolysis reaction is carried out in a regenerative reverse-flow reactor.

FIG. 6 is yet another schematic diagram of an exemplary embodiment of a thermal pyrolysis process in which the thermal pyrolysis reaction is carried out in a regenerative reverse-flow reactor. In this diagram, a distribution device 602 within the reactor 600 may be utilized to provide the quench fluid, which may be the reactive feed, and combine it with the primary pyrolysis product. This distribution device 602 may also provide one of the fuel or oxygen-containing gas during the regeneration/heating step. The distribution device 602 may include a mixing unit, a sparger or conduit with valves and/or nozzles, or other suitable devices, which is configured to provide fuel during the heating step and reactive feed during the pyrolysis step. Beneficially, this distribution device 602 may be utilized to further enhance the process. That is, this device may lessen the void volume within the reactor and provide active quenching to the pyrolysis product in an effective manner once it emerges from the bed packing 608.

In this reactor 600, various valves and lines may be utilized to manage the flow of streams through the reactor 600 (e.g., between locations in the interior region of the housing and external to the interior region). During the heating step, oxidant is provided via line 604 and poppet valve 605, while fuel is introduced via line 606, valve 607 and the distribution device 602. The fuel and oxidant introduced into the first end 610 flow toward the bed packing 608, which is a honeycomb monolith. The mixing zone 612 is the volume between the distribution device 602 and bed packing 608, which is located at a portion of the first end 610. The oxidant and fuel are mixed and combustion is initiated, thereby releasing heat, which is passed to the bed packing 608 as the combustion streams flow toward the second end 614. The combustion products that emerge from the bed packing 608 are passed through the poppet valve 616 into the combustion line 618. During this step, the valves associated with the pyrolysis step are closed to hinder flow of fluid into these lines.

During the pyrolysis step, the pyrolysis feed is introduced into the bed packing 608 via line 620 and poppet valve 622. The pyrolysis stream, which may pass through a distributor (not shown), flows into the different passages of the bed packing 608 from the second end 614 of the reactor 600. Heat is absorbed from the bed packing 608 by the pyrolysis stream, and the primary pyrolysis reaction is carried out producing a primary pyrolysis product. The primary pyrolysis product leaves the bed packing 608 and passes into the mixing zone 612, where it is mixed with a reactive feed being provided via line 625, valve 624 and the distribution device 602. This mixture of these streams results in a secondary pyrolysis reaction that is carried out as the streams interact with each other to produce a secondary pyrolysis product. The secondary pyrolysis product may be conducted away from the reactor 600 via line 626 and poppet valve 628. During this step, the valves associated with the heating step are closed to hinder flow of fluid into these lines.

During pyrolysis, the distribution device 602 provides the reactive feed uniformly over the cross section of the mixing zone allowing it to quickly mix and react with the pyrolysis products that emerge from the bed packing 608. During the regeneration step, the distribution device 602 provides fuel uniformly over the cross section, allowing it to mix and react (or "burn") with the oxidant. In this manner, there is a continuous flow of either quench fluid or fuel through the distribution device 602. A thin layer of refractory coating may be utilized on the outside surfaces of the distribution device 602 to provide insulation, while the flow of fluids inside the distribution device 602 provides cooling of the internal surface of the distribution device 602. In this manner, the distribution device may withstand the high temperatures encountered at this location in the reactor 600.

The different reaction zones may be understood with reference to flow path of the pyrolysis stream. The primary reaction zone may include the volume from the poppet valve 622 and through the bed packing 608. In addition, primary reaction zone may include the volume between the bed packing 608 and the distribution device 602. As noted above, the mixing zone may include the volume between the bed packing 608 and the distribution device 602. The secondary reaction zone may include the volume from the distribution device 602 to the poppet valve 628.

To further describe this process, simulation results, through simulation (Invensys PRO/II), are provided. Referring to FIG. 6 and Table C, the simulation results are associated with the pyrolysis step and do not provide results for the heating step. In this simulation, the primary pyrolysis feedstock is methane, which is referred to as stream S1. Hydrogen is added as stream S2 via recycle from the pyrolysis product (not shown) or another source. The gaseous feed mixture, which is the pyrolysis feed, flows through the heat recuperation zone and into the primary pyrolysis zone, reacting to form the primary pyrolysis product stream S3. The pyrolysis feed (e.g., mixture of streams S1 and S2) may be provided via line 620 to the reactor, while the primary pyrolysis product stream S3 may be the stream that emerges from the bed packing 608. The conditions for stream S3 are 40 psig (276 kPag) and 1650° C. As a result of the pyrolysis reaction, coke is formed as a byproduct that deposits within the bed packing 608 (e.g., the primary pyrolysis zone) and is represented in the simulation as stream S 12. The deposited coke is burned off during the next heating step and conducted away from the reactor via line 618.

The reactive quench stream S8 may be provided via the distribution device 602. The primary pyrolysis product stream S3 and the reactive quench stream S8 mix and react in the secondary pyrolysis zone, forming secondary pyrolysis product stream S10. In this example, the mass flow rate of reactive quench stream S8 is three times the mass flow rate of the hydrocarbon feed to primary pyrolysis stream S1. In Table C, secondary pyrolysis product stream S10 is presented as two different alternatives, as stream S10A and stream SL0B.

Stream S10A is the result of mixing streams S3 and S8 with no reaction, while stream S10B is the same stream after pyrolysis and interconversion reactions. The secondary pyrolysis product stream S10B is mixed with a non-reactive quench stream S13 to form quenched product stream S14. In this example, the non-reactive quench stream is water, and the temperature of the quenched product stream after adiabatic mixing with Stream S10B is 384° C. While this quenching is not shown in the reactor 600, it may be performed downstream of the reactor 600 along the flow path of the stream in line 626. Alternatively, this may be performed within the reactor along the flow path downstream of the distribution is device 602.

As shown in Table C, the stream S10A and stream S10B differ in the resulting temperature based on the reactive or non-reactive composition of the stream. The temperature from the adiabatic mixing of streams S3 and S8 is 867° C., as shown by stream S10A, while the temperature after including

TABLE C

| | | S1 | S2 | S3 | S8 | S10A | S10B | S12 | S13 | S14 |
|---|---|---|---|---|---|---|---|---|---|---|
| | | Methane Feed | Hydrogen Feed | Primary Pyrolysis Product | Reactive Quench (ethane) | Secondary Pyrolysis Product pre-reaction | Secondary Pyrolysis Product post-reaction | Coke Byproduct | Water Quench | Quenched Product |
| Phase | | Vapor | Vapor | Vapor | Vapor | Vapor | Vapor | Solid | Water | Vapor |
| Temperature | ° C. | 30.0 | 30.0 | 1650.0 | 40.0 | 867.0 | 840.1 | 1650.0 | 45.0 | 383.9 |
| Pressure | psig | 40.0 | 40.0 | 40.0 | 130.3 | 40.0 | 40.0 | 40.0 | 50.0 | 40.0 |
| Total Molecular Weight | | 16.04 | 2.02 | 4.42 | 30.07 | 11.19 | 10.88 | 12.01 | 18.02 | 13.08 |
| Flowrate | kg-mol/hr | 1.00 | 2.58 | 4.45 | 1.60 | 6.04 | 6.22 | 0.13 | 2.78 | 9.00 |
| Total Mass Rate | kg/hr | 16.00 | 5.20 | 19.64 | 48.00 | 67.64 | 67.64 | 1.56 | 50.00 | 117.64 |
| Mole Percents | | | | | | | | | | |
| HYDROGEN | | 0.00% | 100.00% | 89.02% | 0.00% | 65.50% | 66.48% | 0.00% | 0.00% | 45.97% |
| METHANE | | 100.00% | 0.00% | 2.51% | 0.00% | 1.84% | 1.79% | 0.00% | 0.00% | 1.24% |
| ETHANE | | 0.00% | 0.00% | 0.00% | 100.00% | 26.42% | 17.12% | 0.00% | 0.00% | 11.84% |
| ETHYLENE | | 0.00% | 0.00% | 0.34% | 0.00% | 0.25% | 14.48% | 0.00% | 0.00% | 10.01% |
| ACETYLENE | | 0.00% | 0.00% | 8.12% | 0.00% | 5.98% | 0.11% | 0.00% | 0.00% | 0.08% |
| BENZENE | | 0.00% | 0.00% | 0.01% | 0.00% | 0.01% | 0.01% | 0.00% | 0.00% | 0.01% |
| H2O | | 0.00% | 0.00% | 0.00% | 0.00% | 0.00% | 0.00% | 0.00% | 100.00% | 30.85% |
| COKE | | 0.00% | 0.00% | 0.00% | 0.00% | 0.00% | 0.00% | 100.00% | 0.00% | 0.00% |
| Weight Percents | | | | | | | | | | |
| HYDROGEN | | 0.00% | 100.00% | 40.62% | 0.00% | 11.80% | 12.32% | 0.00% | 0.00% | 7.09% |
| METHANE | | 100.00% | 0.00% | 9.10% | 0.00% | 2.64% | 2.64% | 0.00% | 0.00% | 1.52% |
| ETHANE | | 0.00% | 0.00% | 0.01% | 100.00% | 70.96% | 47.34% | 0.00% | 0.00% | 27.22% |
| ETHYLENE | | 0.00% | 0.00% | 2.14% | 0.00% | 0.62% | 37.35% | 0.00% | 0.00% | 21.48% |
| ACETYLENE | | 0.00% | 0.00% | 47.87% | 0.00% | 13.90% | 0.26% | 0.00% | 0.00% | 0.15% |
| BENZENE | | 0.00% | 0.00% | 0.26% | 0.00% | 0.07% | 0.07% | 0.00% | 0.00% | 0.04% |
| H2O | | 0.00% | 0.00% | 0.00% | 0.00% | 0.00% | 0.00% | 0.00% | 100.00% | 42.50% |
| COKE | | 0.00% | 0.00% | 0.00% | 0.00% | 0.00% | 0.00% | 100.00% | 0.00% | 0.00% |
| Molar Comp. Rates | kg-mol/hr | | | | | | | | | |
| HYDROGEN | | 0.00 | 2.58 | 3.96 | 0.00 | 3.96 | 4.14 | 0.00 | 0.00 | 4.14 |
| METHANE | | 1.00 | 0.00 | 0.11 | 0.00 | 0.11 | 0.11 | 0.00 | 0.00 | 0.11 |
| ETHANE | | 0.00 | 0.00 | 0.00 | 1.60 | 1.60 | 1.06 | 0.00 | 0.00 | 1.06 |
| ETHYLENE | | 0.00 | 0.00 | 0.01 | 0.00 | 0.01 | 0.90 | 0.00 | 0.00 | 0.90 |
| ACETYLENE | | 0.00 | 0.00 | 0.36 | 0.00 | 0.36 | 0.01 | 0.00 | 0.00 | 0.01 |
| BENZENE | | 0.00 | 0.00 | 0.00 | 0.00 | 0.00 | 0.00 | 0.00 | 0.00 | 0.00 |
| H2O | | 0.00 | 0.00 | 0.00 | 0.00 | 0.00 | 0.00 | 0.00 | 2.78 | 2.78 |
| COKE | | 0.00 | 0.00 | 0.00 | 0.00 | 0.00 | 0.00 | 0.13 | 0.00 | 0.00 |
| Weight Comp. Rates | kg/hr | | | | | | | | | |
| HYDROGEN | | 0.00 | 5.20 | 7.98 | 0.00 | 7.98 | 8.34 | 0.00 | 0.00 | 8.34 |
| METHANE | | 16.00 | 0.00 | 1.79 | 0.00 | 1.79 | 1.79 | 0.00 | 0.00 | 1.79 |
| ETHANE | | 0.00 | 0.00 | 0.00 | 48.00 | 48.00 | 32.02 | 0.00 | 0.00 | 32.02 |
| ETHYLENE | | 0.00 | 0.00 | 0.42 | 0.00 | 0.42 | 25.27 | 0.00 | 0.00 | 25.27 |
| ACETYLENE | | 0.00 | 0.00 | 9.40 | 0.00 | 9.40 | 0.18 | 0.00 | 0.00 | 0.18 |
| BENZENE | | 0.00 | 0.00 | 0.05 | 0.00 | 0.05 | 0.05 | 0.00 | 0.00 | 0.05 |
| H2O | | 0.00 | 0.00 | 0.00 | 0.00 | 0.00 | 0.00 | 0.00 | 50.00 | 50.00 |
| COKE | | 0.00 | 0.00 | 0.00 | 0.00 | 0.00 | 0.00 | 1.56 | 0.00 | 0.00 | reactions is 840° C., as shown by stream S10B. This illustrates that the use of a reactive feed to quench results in a lower temperature leaving the zone than if a non-reactive quench were utilized.

Tables D and E show the converted feedstocks and selectivities to products in the primary and secondary reaction zones. In the primary reaction zone, methane is converted predominantly to acetylene, with a selectivity of about 66%. The selectivity to ethylene is low at about 3%. In the secondary pyrolysis zone, the ethane undergoes endothermic dehydrogenation reactions, as well as interconversion (hydrogen transfer) reactions with the acetylene produced in the primary reaction zone. The overall selectivity to ethylene from the methane and ethane feeds after secondary pyrolysis is about 84%, while the selectivity to acetylene is less than 1%. This example illustrates that the use of a reactive quench increases the selectivity of converted hydrocarbons to desirable ethylene production, while at the same time greatly reducing the concentration of acetylene in the product.

TABLE D

| Yields from Primary Pyrolysis | kg/hr | Product Weight Selectivity |
| --- | --- | --- |
| Methane Converted | 14.21 | |
| Hydrogen product | 2.78 | 19.6% |
| Ethylene product | 0.42 | 3.0% |
| Acetylene product | 9.40 | 66.2% |
| Benzene product | 0.05 | 0.4% |
| Coke byproduct | 1.56 | 11.0% |
| Total | | 100.0% |

TABLE E

| Yields from Primary Plus Secondary Pyrolysis | kg/hr | Weight Selectivity on Primary Plus Secondary Feeds |
| --- | --- | --- |
| Methane Converted | 14.21 | |
| Ethane Converted | 15.98 | |
| Hydrogen product | 3.14 | 10.4% |
| Ethylene product | 25.27 | 83.7% |
| Acetylene product | 0.18 | 0.6% |
| Benzene product | 0.05 | 0.2% |
| Coke byproduct | 1.56 | 5.2% |
| Total | | 100.0% |

In other embodiment, the process may include various configurations.

1. A method for pyrolyzing hydrocarbon in a regenerative pyrolysis reactor, the method comprising the steps of: providing combustion reactants to a mixing zone adjacent a first end of a bed packing in a regenerative pyrolysis reactor; during a first time interval, reacting the combustion reactants to produce heat and combustion products; passing the combustion products through a plurality of passages in the bed packing from the first end to a second end to transfer heat to the bed packing, wherein the bed packing has a plurality of passages through the bed packing from the first end to a second end; conducting away the combustion products from the second end of the bed packing; providing a pyrolysis feed comprising a first hydrocarbon to the second end of the bed packing; and during a second time interval, exposing at least a portion of the pyrolysis feed to peak pyrolysis gas temperatures≥1500° C. and at a pressure of ≥248 kPag as the portion of the pyrolysis feed passes through the bed packing from the second end to the first end to produce a primary pyrolysis product containing unsaturated hydrocarbon, wherein (i) second time interval is less than the first time interval and (ii) the first time interval and the second time interval are combined to be within the range of 1 to 60 seconds.

2. The method of paragraph 1, wherein the pyrolysis feed is comprised of ≤10 wt % $H_2O$, based on the weight of the pyrolysis feed.

3. The method of any one of paragraphs 1 to 2, wherein the pyrolysis feed is comprised of ≤10 mole % $O_2$, based on the weight of the pyrolysis feed.

The principles and modes of operation of this invention have been described above with reference to various exemplary and preferred embodiments. As understood by is those of skill in the art, the overall invention, as defined by the claims, encompasses other preferred embodiments not specifically enumerated herein.

The invention claimed is:

1. A method for pyrolyzing hydrocarbon in a regenerative pyrolysis reactor, the reactor having (i) a mixing zone, (ii) a primary reaction zone, and (iii) a secondary reaction zone, the method comprising the steps of:

providing combustion reactants to the mixing zone, the mixing zone being adjacent a first end of a bed packing located in the primary reaction zone;

during a first time interval, reacting the combustion reactants to produce heat and combustion products;

passing the combustion products through a plurality of passages in the bed packing from the first end to a second end to transfer heat to the bed packing, wherein the bed packing has a plurality of passages through the bed packing from the first end to a second end;

conducting away the combustion products from the second end of the bed packing;

providing a pyrolysis feed comprising a first hydrocarbon to the second end of the bed packing;

during a second time interval, exposing at least a portion of the pyrolysis feed to peak pyrolysis gas temperatures≥1500° C. and at a pressure of≥248 kPag as the pyrolysis feed passes through the bed packing from the second end to the first end to produce a primary pyrolysis product containing unsaturated hydrocarbon, wherein (i) second time interval is less than the first time interval and (ii) the first time interval and the second time interval are combined to be within the range of 1 to 60 seconds;

injecting a reactive feed comprising a second hydrocarbon into the secondary reaction zone to mix with the primary pyrolysis product and produce a secondary pyrolysis product, wherein the secondary pyrolysis product has an ethylene concentration greater than that of the primary pyrolysis product; and removing the secondary pyrolysis product from the regenerative pyrolysis reactor.

2. The method of claim 1, wherein the reactive feed comprises at least 50 wt % ethane, based on total weight of the reactive feed.

3. The method of claim 1, further comprising providing the reactive feed at a temperature≤500° C.

4. The method of claim 1, wherein the reactive feed is injected into the regenerative pyrolysis reactor and the pyrolysis feed is provided at a respective mass flow ratio of from 0.5:1 to 2.0:1, based on the mass of the hydrocarbon in the reactive feed and pyrolysis feed.

5. The method of claim 1, wherein the unsaturated hydrocarbon in the secondary pyrolysis product is comprised of>50 wt % ethylene compounds, based on total weight of the unsaturated hydrocarbon.

6. The method of claim 1, wherein the secondary pyrolysis product comprises of ethylene and acetylene at a respective mass ratio of≥1.5:1 based on the weight percentage of ethylene and acetylene in the secondary pyrolysis product.

7. The method of claim 1, wherein the first hydrocarbon and the second hydrocarbon are different mixtures of hydrocarbons.

8. The method of claim 1, wherein the sum of the first time interval and the second time interval is in the range of 1 to 30 seconds.

9. The method of claim 1, wherein the sum of the first time interval and the second time interval is in the range of 1 to 15 seconds.

10. The method of claim 1, wherein the primary pyrolysis product has an ethylene to acetylene (E/A) weight ratio≥0.2.

11. The method of claim 1, wherein the primary pyrolysis product is exposed to a peak pyrolysis gas temperature of at least 1600° C.

12. The method of claim 1, wherein the secondary pyrolysis product is exposed to a peak pyrolysis gas temperature that is less than the peak pyrolysis gas temperature at which the primary pyrolysis product is exposed.

13. The method of claim 1, wherein the secondary pyrolysis product is contacted with a quench fluid to cool the secondary pyrolysis product.

14. The method of claim 1, wherein the primary pyrolysis product is contacted with a quench fluid to cool the primary pyrolysis product.

15. The method of claim 1, wherein the pyrolysis reactor is operated at a pressure in the range of 248 kPag to 2068 kPag.

16. The method of claim 1, wherein the pyrolysis reactor is operated at a pressure in the range of 303 kPag to 1124 kPag.

* * * * *